(12) United States Patent
Berry et al.

(10) Patent No.: US 7,309,358 B2
(45) Date of Patent: *Dec. 18, 2007

(54) VERTEBRAL BODY AND DISC SPACE REPLACEMENT DEVICES

(75) Inventors: Bret M. Berry, Cordova, TN (US); Eric C. Lange, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 481 days.

This patent is subject to a terminal disclaimer.

(21) Appl. No.: 10/400,837

(22) Filed: Mar. 27, 2003

(65) Prior Publication Data

US 2003/0191531 A1 Oct. 9, 2003

Related U.S. Application Data

(63) Continuation-in-part of application No. 10/103,237, filed on Mar. 21, 2002, now Pat. No. 6,758,862.

(51) Int. Cl.
*A61F 2/44* (2006.01)

(52) U.S. Cl. ...................... 623/17.16; 606/61
(58) Field of Classification Search ............. 606/61; 623/17.11, 17.12, 17.13, 17.14, 17.15, 17.16
See application file for complete search history.

(56) References Cited

U.S. PATENT DOCUMENTS

| | | | |
|---|---|---|---|
| 2,677,369 A | 5/1954 | Knowles | |
| 4,309,777 A | 1/1982 | Patil | |
| 4,599,086 A | 7/1986 | Doty | |
| 4,820,305 A | 4/1989 | Harms et al. | |
| 4,834,757 A | 5/1989 | Brantigan | |
| 5,062,850 A | 11/1991 | MacMillan et al. | |
| 5,147,404 A | 9/1992 | Downey | |
| 5,192,327 A | 3/1993 | Brantigan | |
| 5,397,364 A * | 3/1995 | Kozak et al. ............ 623/17.11 |
| 5,443,515 A | 8/1995 | Cohen et al. | |
| 5,458,638 A | 10/1995 | Kuslich et al. | |
| 5,458,641 A | 10/1995 | Ramirez Jimenez | |
| 5,534,029 A | 7/1996 | Shima | |
| 5,571,190 A | 11/1996 | Ulrich et al. | |
| 5,609,635 A | 3/1997 | Michelson | |
| 5,609,637 A | 3/1997 | Biedermann et al. | |
| 5,702,451 A | 12/1997 | Biedermann et al. | |
| 5,702,455 A | 12/1997 | Saggar | |
| 5,776,199 A | 7/1998 | Michelson | |
| 5,782,832 A | 7/1998 | Larsen et al. | |
| 5,861,041 A | 1/1999 | Tienboon | |
| 5,865,845 A | 2/1999 | Thalgott | |
| 5,897,556 A | 4/1999 | Drewry et al. | |

(Continued)

FOREIGN PATENT DOCUMENTS

DE 197 38 052 A1 3/1999

*Primary Examiner*—Cris Rodriguez
*Assistant Examiner*—Candice C. Stokes
(74) *Attorney, Agent, or Firm*—Krieg DeVault LLP

(57) ABSTRACT

A vertebral replacement body device for supporting adjacent vertebrae includes a connecting member having an upper member and a lower member engaged thereto at opposite ends thereof. The members can be restrained relative to one another to resist axial, rotation and/or lateral displacement. The vertebral replacement body device can have a chamber extending therethrough for fusion of the supported vertebrae.

80 Claims, 23 Drawing Sheets

U.S. PATENT DOCUMENTS

| | | |
|---|---|---|
| 5,972,031 A | 10/1999 | Biedermann et al. |
| 5,989,290 A | 11/1999 | Biedermann et al. |
| 6,086,613 A | 7/2000 | Camino et al. |
| 6,102,949 A | 8/2000 | Biedermann et al. |
| 6,106,557 A | 8/2000 | Robioneck et al. |
| 6,159,211 A | 12/2000 | Boriani et al. |
| 6,200,348 B1 | 3/2001 | Biedermann et al. |
| 6,241,771 B1 | 6/2001 | Gresser et al. |
| 6,245,108 B1 | 6/2001 | Biscup |
| 6,296,665 B1 | 10/2001 | Struad et al. |
| 6,409,765 B1 * | 6/2002 | Bianchi et al. .......... 623/17.11 |
| 6,454,806 B1 | 9/2002 | Cohen et al. |
| 6,758,862 B2 | 7/2004 | Berry et al. |
| 2002/0099444 A1 | 7/2002 | Boyd et al. |
| 2002/0120334 A1 * | 8/2002 | Crozet ..................... 623/17.11 |
| 2002/0120338 A1 | 8/2002 | Boyer, II et al. |
| 2002/0161443 A1 * | 10/2002 | Michelson ............... 623/17.11 |
| 2003/0009235 A1 | 1/2003 | Manrique et al. |
| 2003/0125739 A1 | 7/2003 | Bagga et al. |
| 2003/0176925 A1 * | 9/2003 | Paponneau ............... 623/17.16 |
| 2004/0073314 A1 | 4/2004 | White et al. |
| 2004/0236427 A1 | 11/2004 | Berry et al. |

* cited by examiner

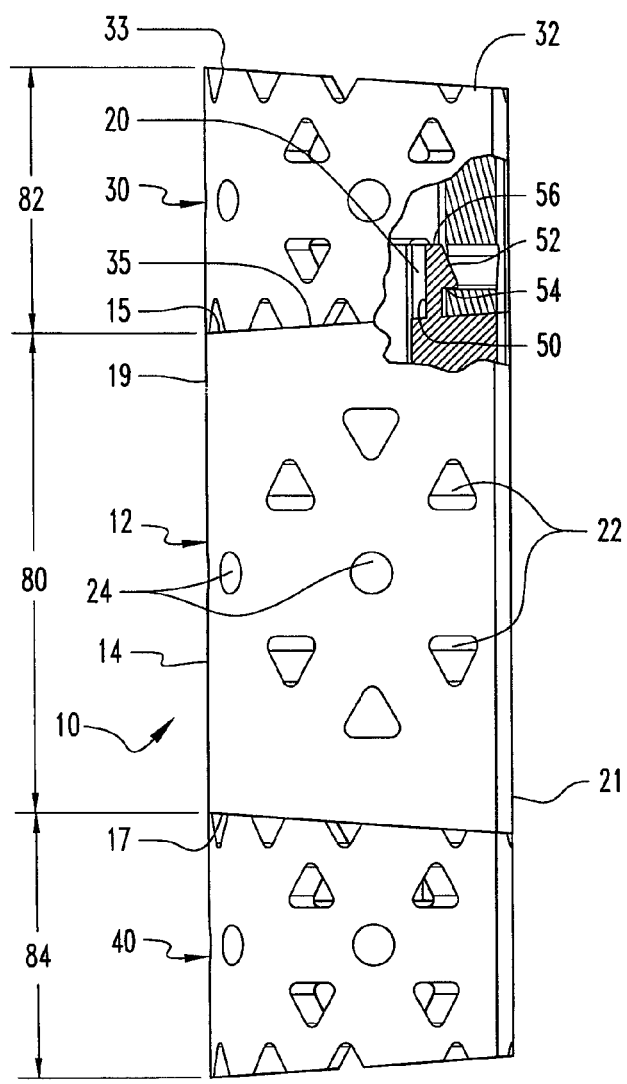
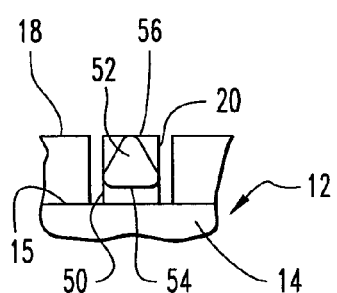
Fig. 4
Fig. 3

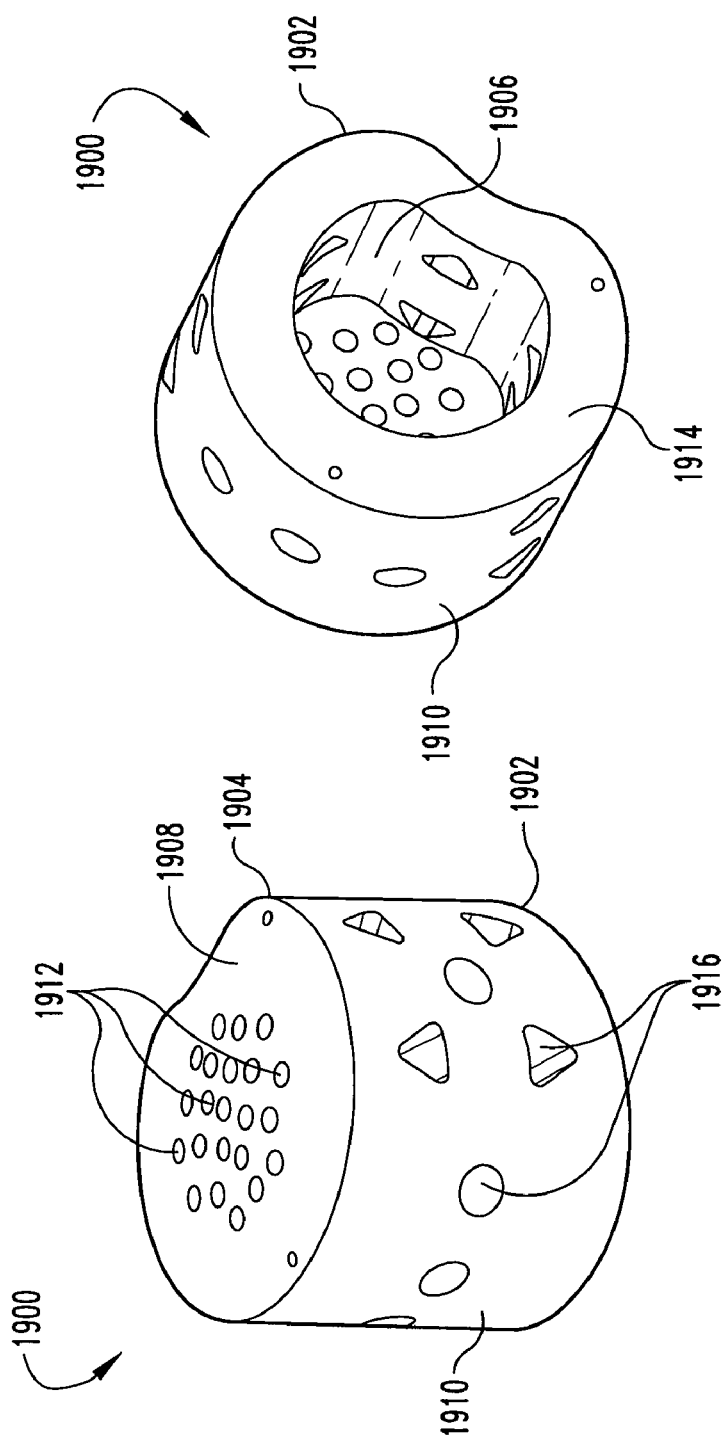

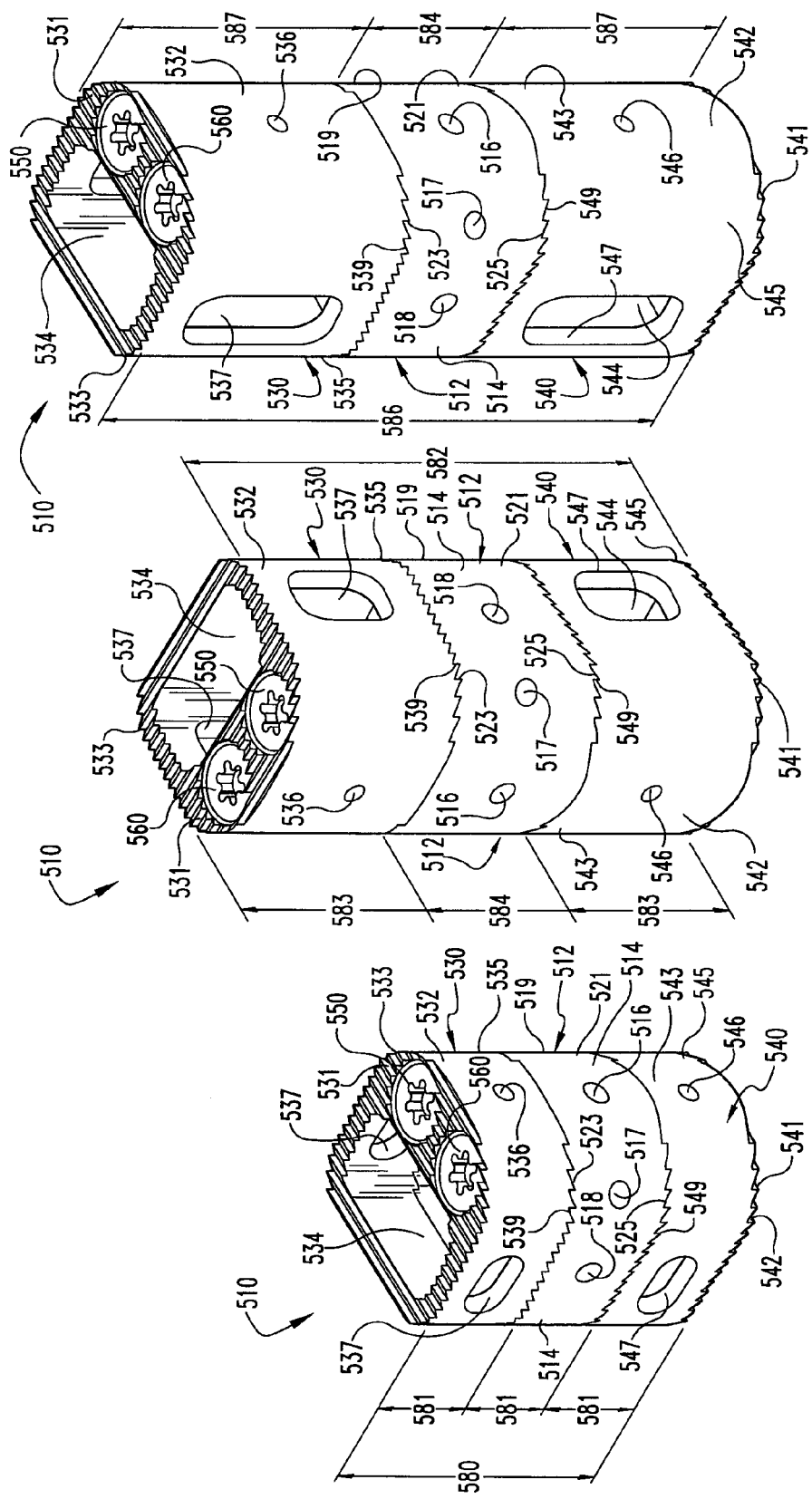

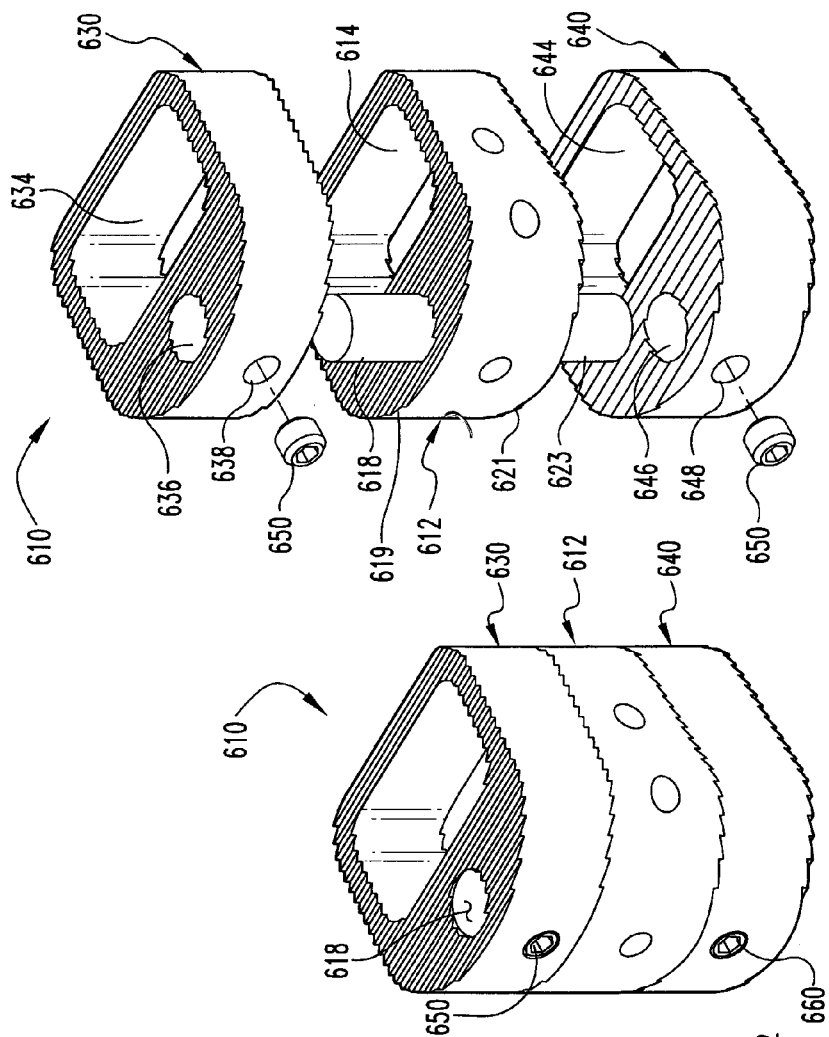
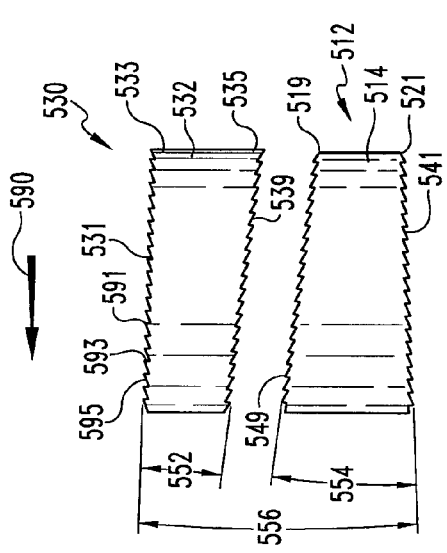
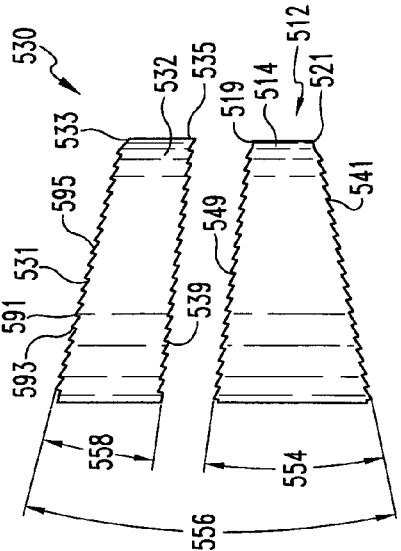
Fig. 29
Fig. 28
Fig. 27A
Fig. 27B

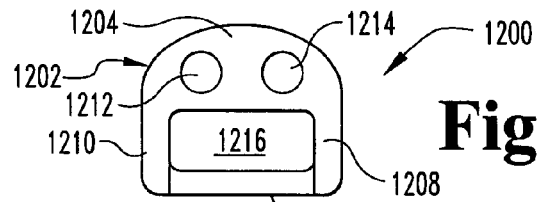
Fig. 37
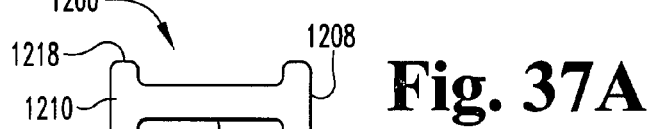
Fig. 37A
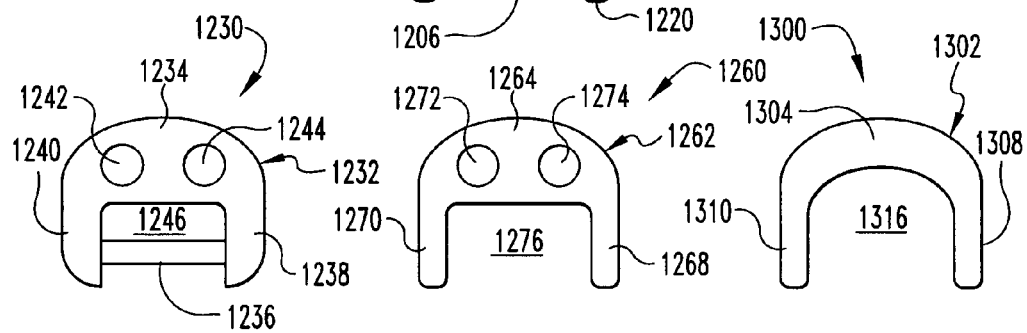
Fig. 38  Fig. 39  Fig. 40
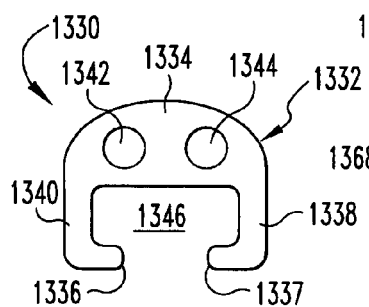
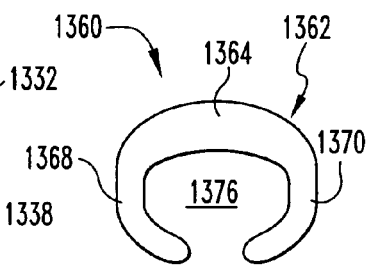
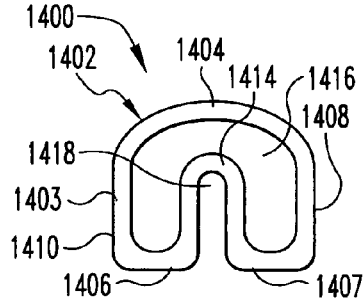
Fig. 41  Fig. 42  Fig. 43
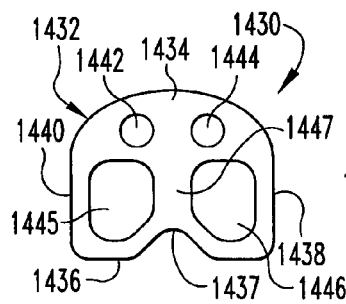
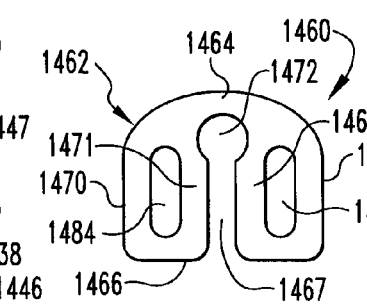
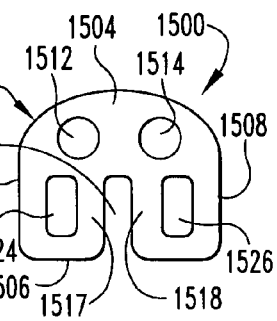
Fig. 44  Fig. 45  Fig. 46

VERTEBRAL BODY AND DISC SPACE REPLACEMENT DEVICES

CROSS-REFERENCE TO RELATED APPLICATION

The application is a continuation-in-part application of U.S. patent application Ser. No. 10/103,237 filed on Mar. 21, 2002, and now issued as U.S. Pat. No. 6,758,862.

BACKGROUND

The present invention is directed to devices for replacement of one or more vertebral bodies and/or one or more disc spaces between vertebrae of a spinal column.

The repair and reconstruction of bony structures is sometimes accomplished by directly fixing adjacent bony structures to each other, such as by a plate. In other instances, bone growth inducing material can be introduced between the adjacent bony structures, which over time results in a solid bony connection. In some instances, the adjacent bony structures are not sufficiently strong to maintain their patency as the bone heals or the bone grows between the adjacent structures through the bone growth inducing material. In these instances, mesh structures or cages have been provided to engage the adjacent bony structures to provide additional stability. The cages are generally hollow and can be configured to contact the harder cortical bone of the adjacent bony structures. The hollow portion of the cages can be filled with bone growth inducing material.

There remains a need for improved devices for replacing one or more vertebral bodies and/or one or more disc spaces in a spinal column. The present invention is directed to satisfying these needs, among others.

DESCRIPTION OF THE FIGURES

FIG. 3 is a side elevation view of the vertebral replacement device of FIG. 1 in partial section to illustrate the interconnection between adjacent members of the device.

FIG. 4 is an elevational view of an engaging member comprising a portion of the vertebral body member of the device of FIG. 1.

FIG. 22 is a perspective view of another embodiment disc replacement member usable with a vertebral replacement device.

FIG. 23 is another perspective view of the disc replacement member of FIG. 22.

FIG. 24 is a perspective view of another embodiment vertebral replacement device.

FIG. 25 is a perspective view of another embodiment vertebral replacement device.

FIG. 26 is a perspective view of another embodiment vertebral replacement device.

FIGS. 27A and 27B are side views of another embodiment vertebral replacement device.

FIG. 28 is a perspective view of another embodiment vertebral replacement device.

FIG. 29 is an exploded perspective view of the vertebral replacement device of FIG. 28.

FIGS. 37 and 37A are a plan view and elevation view, respectively, of another embodiment vertebral replacement device.

FIG. 38 is a plan view of a member of another embodiment vertebral replacement device.

FIG. 39 is a plan view of a member of another embodiment vertebral replacement device.

FIG. 40 is a plan view of a member of another embodiment vertebral replacement device.

FIG. 41 is a plan view of a member of another embodiment vertebral replacement device.

FIG. 42 is a plan view of a member of another embodiment vertebral replacement device.

FIG. 43 is a plan view of a member of another embodiment vertebral replacement device.

FIG. 44 is a plan view of a member of another embodiment vertebral replacement device.

FIG. 45 is a plan view of a member of another embodiment vertebral replacement device.

FIG. 46 is a plan view of a member of another embodiment vertebral replacement device.

DESCRIPTION OF THE ILLUSTRATED EMBODIMENTS

Figure 1:
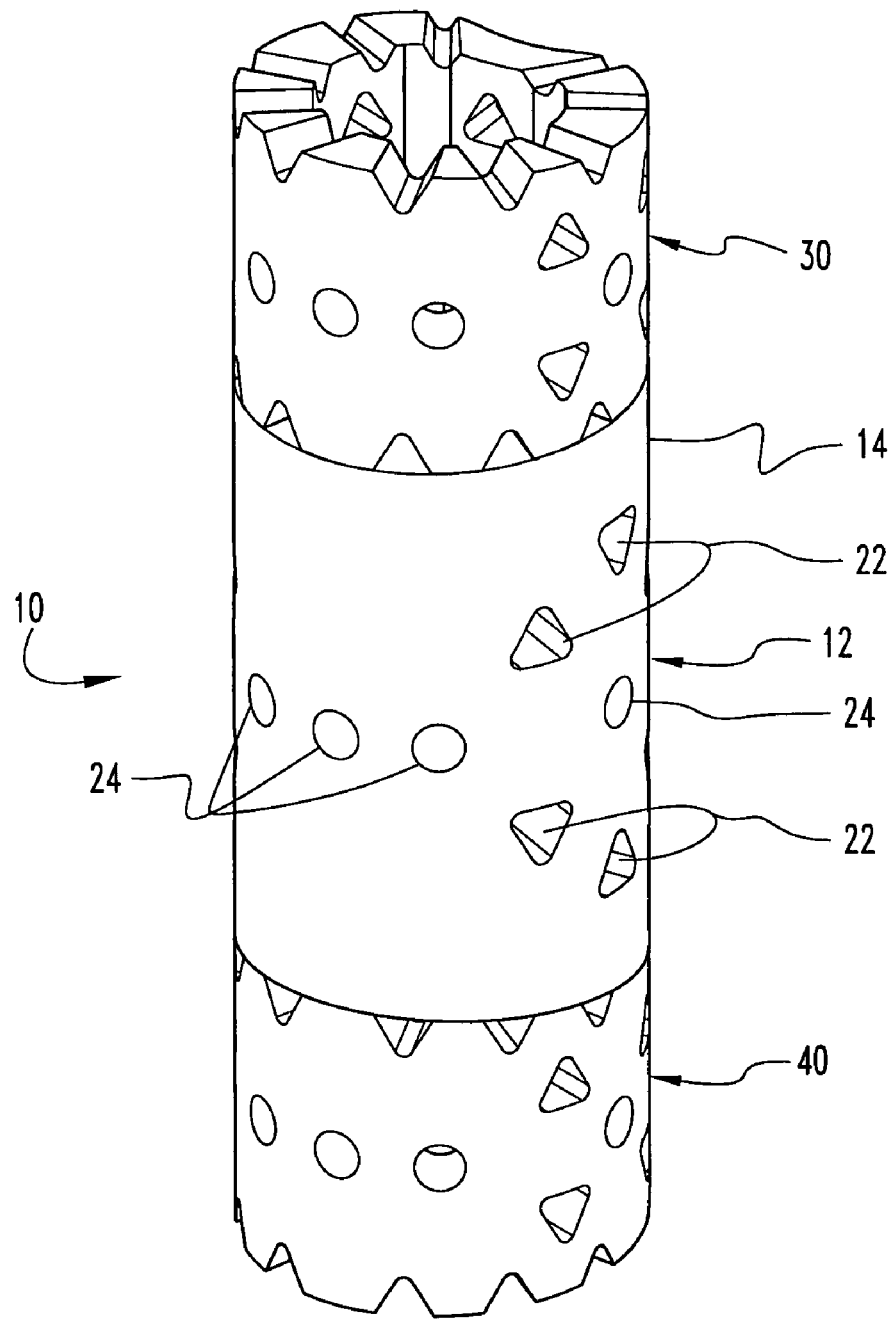
FIG. 1 is a perspective view of a vertebral replacement device according to one embodiment.

For the purpose of promoting an understanding of the principles of the invention, reference will now be made to the illustrated embodiments thereof and specific language will be used to describe the same. It will nevertheless be understood that no limitation of the scope of the invention is thereby intended. Any such alterations and further modifications in the invention, and any such further applications of the principles of the invention as described herein are contemplated as would normally occur to one skilled in the art to which the invention relates.

The present invention relates to devices for replacing one or more vertebral bodies in the spinal column and/or one or more disc spaces between adjacent vertebrae. It is contemplated that the replacement devices will support adjacent ones of the intact vertebrae during fusion thereof. It is further contemplated that one or more members of the vertebral replacement devices can be positioned in a disc space between adjacent vertebrae for supporting the adjacent vertebrae during fusion thereof.

In one embodiment, the device can employ current mesh or cage-type devices for engagement with adjacent bony structures, although other types of bone supporting devices are also contemplated. The vertebral replacement device can have a tubular form with a hollow chamber extending therethrough. The adjacent vertebrae are supported by opposite ends of the device and the chamber can be filled with bone growth inducing or osteogenetic material. The ends of the device can include flattened plateau-like end surfaces that can be formed at the junction between bars defining the mesh wall structure of the device.

In one embodiment, the vertebral replacement device includes a connecting member and an upper attached to an upper end of the connecting member and a lower member attached to a lower end of the connecting member. Each of the members can have a generally kidney bean cross-sectional shape in the plane transverse to the central axis of the assembled device. Other cross-sectional shapes are also contemplated, including circular, racetrack-shaped, rectangular, square, oval, D-shaped, triangular, boomerang, banana, or other polygonal shape. Each of the upper and lower members can include an interior chamber. The connecting member can also include an interior chamber that generally aligns with the interior chambers of the upper and lower members engaged thereto.

In one embodiment, the upper and lower members can be fabricated from a tubular mesh having apertures through its wall. One example of a tubular mesh is provided in U.S. Pat. No. 5,897,556, which is incorporated herein by reference in its entirety. The connecting member can also be fabricated from a tubular mesh. Further forms contemplate that the upper and lower members and connecting member can be a tubular body with solid walls or wall structure including one or more openings.

In one embodiment, the upper and lower members can be telescopically and non-rotatably engaged with the connecting member. The connecting member includes an upper extension and a lower extension extending therefrom. The upper and lower extensions are in the form of substantially continuous rings extending around the respective ends of the vertebral body or connecting member. Other forms for the upper and lower extensions are also contemplated. The upper and lower extensions are received in the interior chamber of the respective upper or lower members when the upper and lower members are engaged to the connecting member. In another embodiment, extensions are provided on the upper and lower members, and these extensions are received in an interior chamber or opening at respective ends of the connecting member.

Each of the upper and lower extensions, and each of the chambers of the upper and lower members, can have a non-circular cross-section and interface to prevent relative rotation between the connecting member and the upper or lower member engaged thereto.

In one embodiment, the upper and lower extensions of the connecting member each include an engaging member which can be flexed inwardly as the respective upper or lower member is placed around the respective extension of the connecting member. The engaging member fits into an opening or aperture in the inner wall surface of the respective upper and lower members to axially secure the respective upper and lower members to the connecting member.

The vertebral replacement device can be made from any biocompatible material, including synthetic or natural autograft, allograft or xenograft tissues, and can be resorbable or non-resorbable in nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are non-reinforced polymers, carbon-reinforced polymer composites, PEEK and PEEK composites, shape-memory alloys, titanium, titanium alloys, cobalt chrome alloys, stainless steel, ceramics and combinations thereof and others as well.

Any suitable osteogenetic material or composition is contemplated for placement within the chambers defined by the members of the vertebral replacement device. Such osteogenic material includes, for example, autograft, allograft, xenograft, demineralized bone, synthetic and natural bone graft substitutes, such as bioceramics and polymers, and osteoinductive factors. Where bony material is placed within the chambers of the members of the vertebral replacement device, the material can be pre-packed into the hollow chambers before the device is implanted, or can be pushed through the plurality of wall openings after the device is in position in the spinal column. A separate carrier to hold the materials within the chambers of the device can also be used. These carriers can include collagen-based carriers, bioceramic materials, such as BIOGLASS®, hydroxyapatite and calcium phosphate compositions. The carrier material can be provided in the form of a sponge, a block, folded sheet, putty, paste, graft material or other suitable form. Moreover, the osteogenetic compositions contained within the vertebral replacement device can comprise an effective amount of a bone morphogenetic protein, transforming growth factor β1, insulin-like growth factor 1, platelet-derived growth factor, fibroblast growth factor, LIM mineralization protein (LMP), and combinations thereof or other therapeutic or infection resistant agent, held within a suitable carrier material.

Figure 2:
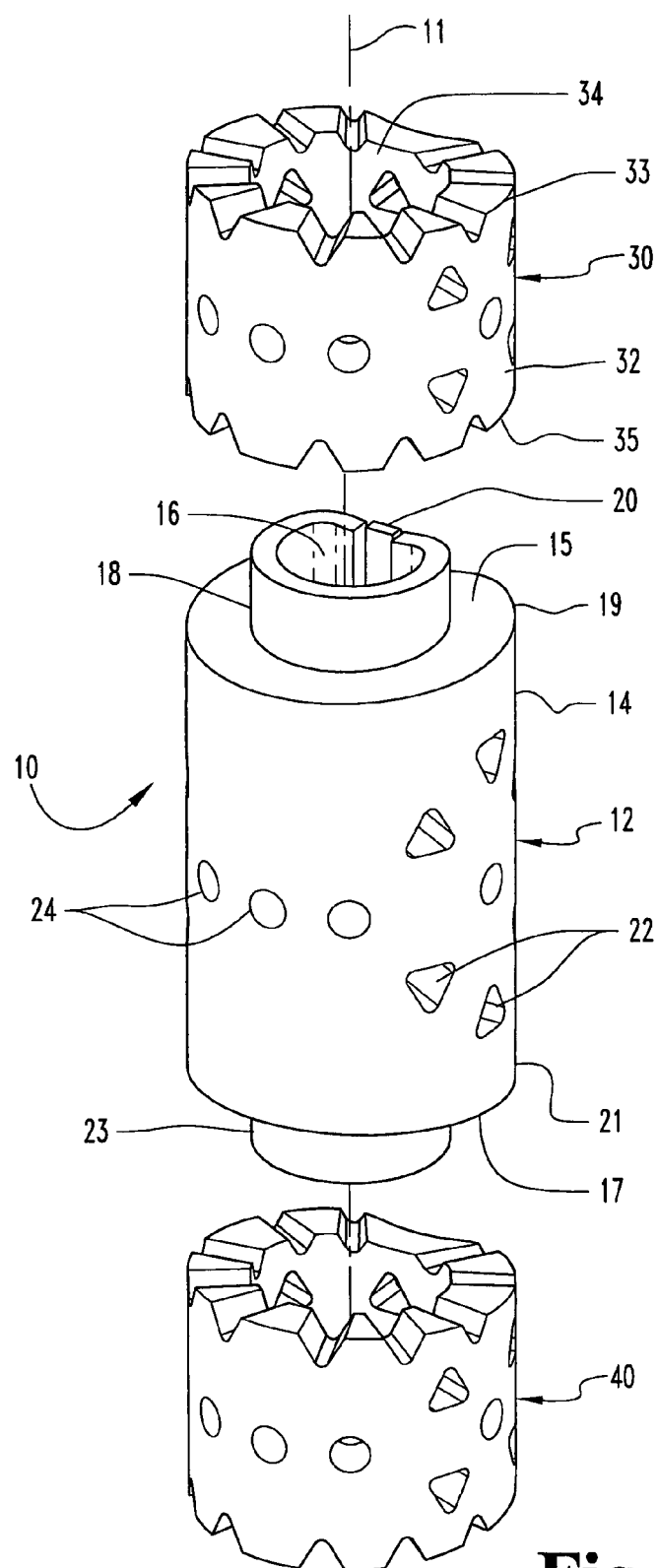
FIG. 2 is an exploded perspective view of the vertebral replacement device of FIG. 1.

In FIGS. 1-2, a vertebral replacement device 10 includes a connecting member 12, an upper member 30, and a lower member 40. Device 10 is illustrated as having a tubular form that extends along a longitudinal axis 11 and defines a chamber extending therethrough along axis 11. Bone growth can occur through this chamber for fusion between the vertebral bodies supported at each end of device 10.

Connecting member 12 includes a body 14 extending between an upper end 19 and an opposite lower end 21. Connecting member 12 further includes an upper extension 18 and a lower extension 23. Connecting member 12 has an inner wall surface 13 (FIG. 5) that defines a chamber 16 extending between and opening at the outer ends of the extensions 18, 23. Each of the extensions 18, 23 extends outwardly from the respective end 19, 21 of body 14 and around chamber 16. End surface 15 extends around upper extension 18, and end surface 17 extends around lower extension 23. In the illustrated embodiment, extensions 18, 23 are substantially continuous rings extending from their respective end 19, 21. Other embodiments contemplate other forms for the extensions, such as, for example, a series of two or more flexible engaging members (such as engaging member 20 discussed below) or rigid engaging members.

The wall of body 14 includes a number of triangular apertures 22 which extend through the wall and communicate with chamber 16. Other shapes for apertures 22 are also contemplated, including non-circular shapes such as a square, diamond, oval and/or rectangular shapes, circular shapes, and/or polygonal shapes. The wall of body 14 also includes a number of holes 24 extending at least partially therethrough. Holes 24 can be threaded or otherwise sized and/or configured for engagement with one or more insertion instruments (not shown.)

Figure 5:
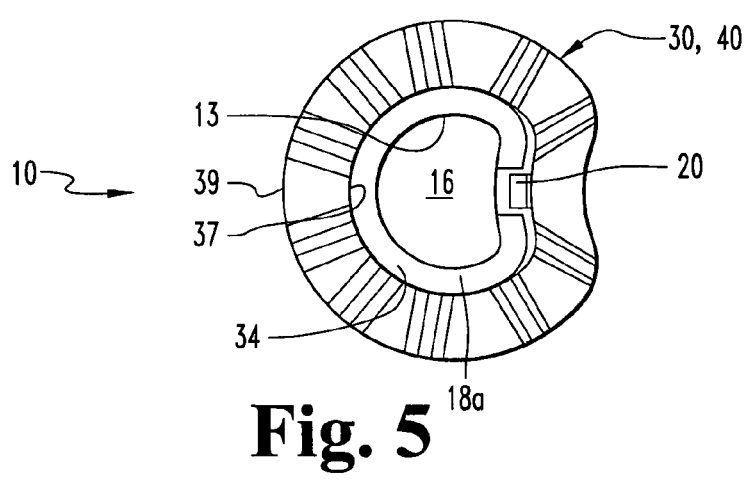
FIG. 5 is an end view of the vertebral replacement device of FIG. 1.

Referring further to FIGS. 3-5, the substantially continuous wall of each of the extensions 18, 23 is interrupted by an engaging member 20. Only engaging member 20 for upper extension 18 is illustrated, it being understood that lower extension 23 call also be provided with an identical or similar engaging member. Engaging members 20 secure upper member 30 and lower member 40 to respective ends of connecting member 12, resisting axial dislocation of upper member 30 and lower member 40 away from connecting member 12 along axis 11. Engaging members 20 can also resist axial rotation of upper and lower members 30, 40 relative to connecting member 12 about axis 11. Other embodiments contemplate that more than one engaging member 20 is provided in the wall of one or both of the extensions 18, 23. Further embodiments contemplate that wall of one or both of the extensions 18, 23 is not substantially continuous, but rather is continuous or includes a number of discrete wall portions sufficiently spaced and sized about body 14 of connecting member 12 for engagement with upper and lower members 30, 40.

Engaging member 20 includes a projection or engaging portion 52 and a stem 50 connected or integrally formed with end surface 15 of body 14. Stem 50 has a reduced thickness to allow engaging member 20 to deflect inwardly in response to a force applied to engaging portion 52. Engaging portion 52 projects outwardly from stem 50 and has a triangular shape tapering from an engaging surface 54 to an upper end 56. Other configurations for engaging member 20 are also contemplated. For example, engaging member 20 can be provided with an engaging portion 52 in the form of a partially spherical or rounded nub, a receptacle, rectangular or polygonal shaped tab or projection. Engaging portion 52 can also correspond to the shape the aperture 22 in which it is received. Engaging member 20 can also be a snap ring, collet, bayonet lock, or surface irregularity that resists axial movement of the engaged upper member 30 and lower member 40 away from connecting member 12 along axis 11.

Figure 6:
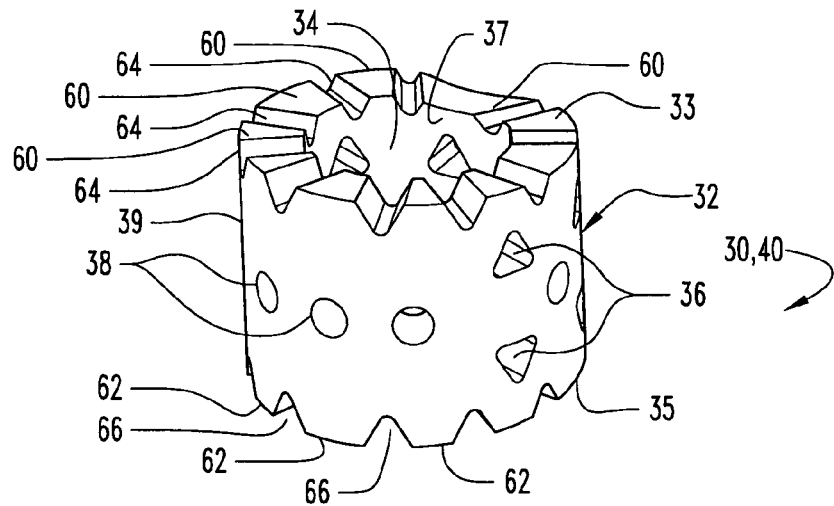
FIG. 6 is a perspective view of a member comprising a portion of the vertebral replacement device of FIG. 1.
Figure 7:
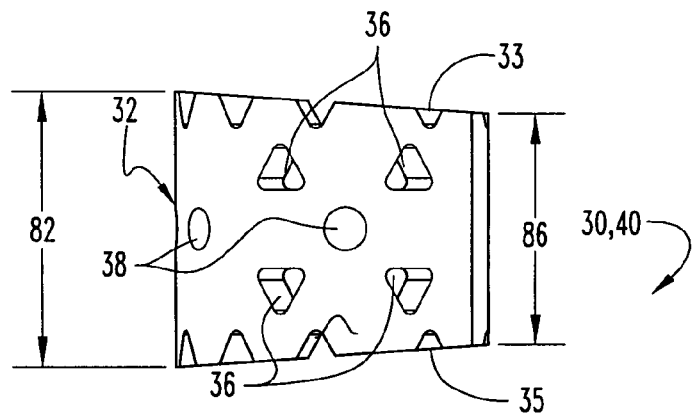
FIG. 7 is an elevation view of the member of FIG. 6.

Referring also to FIGS. 6-7, upper and lower members 30, 40 are illustrated as being identical, although it is also contemplated that upper member 30 and lower member 40 can be provided with different configurations and/or sizes. With respect to FIGS. 6 and 7, only upper member 30 will be further described, it being understood that lower member 40 can be provided with identical features.

Upper member 30 includes a body 32 extending between an upper end 33 and a lower end 35. Body 32 has a height 82 between the upper and lower ends 33, 35. Height 82 can be selected so that upper member 30 fits within an intervertebral disc space between adjacent vertebrae. Upper end 33 and lower end 35 can be sloped to converge toward one another and form a height 86 opposite height 82. The sloped ends 33, 35 allow upper member 30 to restore and/or conform to the natural inclination between the adjacent endplates of the vertebral bodies. It is further contemplated that ends 33, 35 can be parallel to one another.

Body 32 has an inner wall surface 37 defining a chamber 34 that extends between and opens at ends 33, 35. As shown in FIG. 5, body 32 has an outer surface 39 that defines a kidney-shaped cross section transverse to longitudinal axis 11. Other cross-sectional shapes are also contemplated, including, for example, circular cross-sections and non-circular cross-sections, such as oval, triangular, square, rectangular, polygonal, boomerang shaped, D-shaped, or racetrack shaped cross-sections. In the illustrated embodiment, connecting member 12 has the same cross-sectional shape as the upper and lower members 30, 40 to provide a vertebral replacement body device of uniform cross-sectional shape and size along its height.

Body 32 defines a number of triangular apertures 36 extending at least partially therethrough in communication with chamber 34, and a number of circular holes 38 extending at least partially therethrough from the exterior surface of body 32. Holes 38 or the other holes can be threaded or otherwise sized and/or configured for engagement with one or more insertion instruments.

Body 32 further includes a number of bearing surfaces 60 spaced around first end 32 and bearing surfaces 62 spaced around second end 35. Adjacent ones of each of the bearing surfaces 60 are separated from one another by V-shaped recesses 64. Adjacent ones of each of the bearing surfaces 62 are separated from one another by V-shaped recesses 66. Bearing surfaces 60, 62 are planar and provide a number of plateau-like, generally flat bearing surfaces spaced about the respective end of body 32. Bearing surfaces 60, 62 have a trapezoidal shape in the illustrated embodiment, although other shapes are also contemplated. In the illustrated embodiment, ten such bearing surfaces 60, 62 are provided at each end of body 32. It is also contemplated that fewer than ten or more than ten bearing surfaces could be provided. It is further contemplated that each end of body 32 could be provided with a single, continuous bearing surface extending around chamber 34.

The plateau-like bearing surfaces 60, 62 provide a surface area about the ends of body 32 for bearing support of the adjacent vertebral endplate and to resist subsidence of body 32 into the vertebrae. The plateau-like bearing surfaces 60, 62 provide surface area contact between the end of body 32 and the adjacent endplate, providing frictional resistance to body 32 sliding or twisting relative to the adjacent vertebral endplate.

Upper member 30 and lower member 40 are connected to respective ends of connecting member 12 to provide vertebral replacement body device 10. Upper member 30 is advanced over upper extension 18 so that upper extension 18 extends into chamber 34. Engaging member 20 flexes inwardly as inner wall surface 37 of body 32 passes along engaging portion 52. Engaging portion 52 is configured to reside within one of the apertures 36 extending into the wall of body 32 from chamber 34. When engaging portion 52 and the respective aperture 36 are aligned, engaging member 20 returns towards its pre-insertion position with engaging portion 52 residing in the respective aperture 36. This engages upper member 30 to connecting member 12, resisting movement of upper member 30 away from connecting member 12 along axis 11. It is further contemplated engaging surface 54 engages the adjacent lower surface of the respective aperture 36 to provide a positive seat between bearing surface 15 of connecting member 12 and bearing surfaces 62 about end 33 of upper member 30. Lower member 40 is secured to lower extension 23 in a similar manner.

Bearing surfaces 62 at lower end 35 of upper member 30 bear against end surface 15 extending about upper extension 18 of connecting member 12. This bearing relationship transmits the spinal column load from upper member 30 to connecting member 12. The bearing surfaces of the lower member 40 similarly bear against end surface 17 extending about lower extension 23 of connecting member 12. The end surfaces 15, 17 at the ends of body 14 and the adjacent bearing surfaces of the upper and lower members 30, 40 do not interdigitate. This bearing relationship eliminates stress concentrations and shifting of the components of device 10 that might result from improperly aligned interdigitating surfaces.

Axial rotation of upper member 30 and lower member 40 relative to connecting member 12 is resisted by the interface between upper and lower extensions 18, 23 and the respective inner wall surface of the upper and lower members 30, 40. In the illustrated embodiment, extensions 18, 23 have a non-circular shape, such as the kidney shape shown in FIG. 5. Similarly, the inner wall surface 37 of upper member 30 and also the inner wall surface of lower member 40 have a non-circular-shape sized to receive in form fitting engagement the respective upper or lower extension 18, 23. This noncircular form fitting engagement prevents rotation of upper member 30 and lower member 40 relative to connecting member 12.

Device 10 can be used to replace a vertebra that has been removed from the spinal column segment using known techniques. Device 10 is assembled by securing upper member 30 to one end of connecting member 12 and securing lower member 40 to the other end of connecting member 12. This provides a vertebral replacement device 10 that has an overall height that is equal to the sum of the heights 80 of body 14, height 82 of upper member 30, and height 84 of lower member 40 (FIG. 3.)

Figure 8:
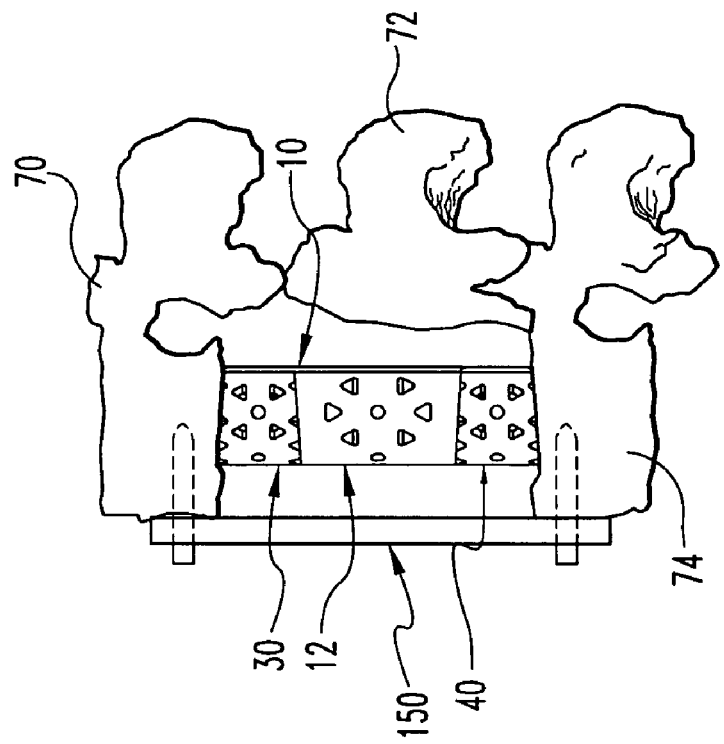
FIG. 8 is an elevational view of the vertebral replacement device of FIG. 1 positioned in the spinal column between two vertebrae.

As shown in FIG. 8, the vertebral replacement device 10 can be placed between vertebra 70 and vertebra 74 after removal of vertebra 72. Replacement of more than one vertebra is also contemplated. Although not required, it is contemplated that height 80 could be representative of that of the removed vertebra and heights 82, 84 could be representative of the heights of the respective disc spaces between the removed vertebra 72 and the remaining vertebrae 70, 74. Also shown in FIG. 8 is a stabilization construct 150 engaged to and extending between vertebrae 70 and 74 to support and stabilize the spinal column segment before, during and, if construct 150 is non-resorbable and left in the patient, after fusion. Stabilization construct 150 can be a rod system, plate system or artificial ligament system. It is further contemplated that stabilization system could be attached to any portion of vertebrae 70 and 74, including the anterior, antero-lateral, lateral, postero-lateral or posterior portions.

It is also contemplated that heights 82 and 84 could be identical or different, and that the ends of upper and lower members 30, 40 could be provided with the same or differing angles of inclination. It is further contemplated that device 10 can comprise a kit having a number of upper members 30 and lower members 40 of various sizes and heights 82, 84. A kit could also include a number of connecting members 12 of various sizes and heights 80. Such a kit would provide the surgeon flexibility in selecting the appropriately size and height for members of a device 10 based on conditions encountered in surgery.

Figure 9:
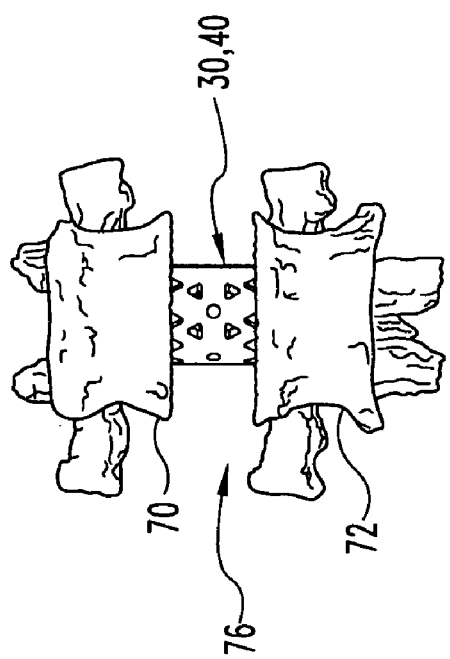
FIG. 9 is an elevational view of one of the members comprising a portion of the vertebral replacement device of FIG. 1 positioned in a spinal disc space between adjacent vertebrae.

FIG. 9 illustrates placement of one of the upper or lower members 30, 40 in disc space 76 between adjacent vertebrae 70, 72 to function as an interbody fusion device. Engagement of stabilization construct to vertebrae 70 and 72 is also contemplated.

It is also contemplated that connecting member 12 could be provided with one end configured to bear against a vertebral endplate, and that only one of the upper and lower members 30, 40 is engaged to the other end of connecting member 12. The assembled device could then be placed between adjacent vertebrae with an end of connecting member 12 and an end of the selected upper or lower member 30, 40 in contact with the adjacent vertebral endplates.

Figure 10:
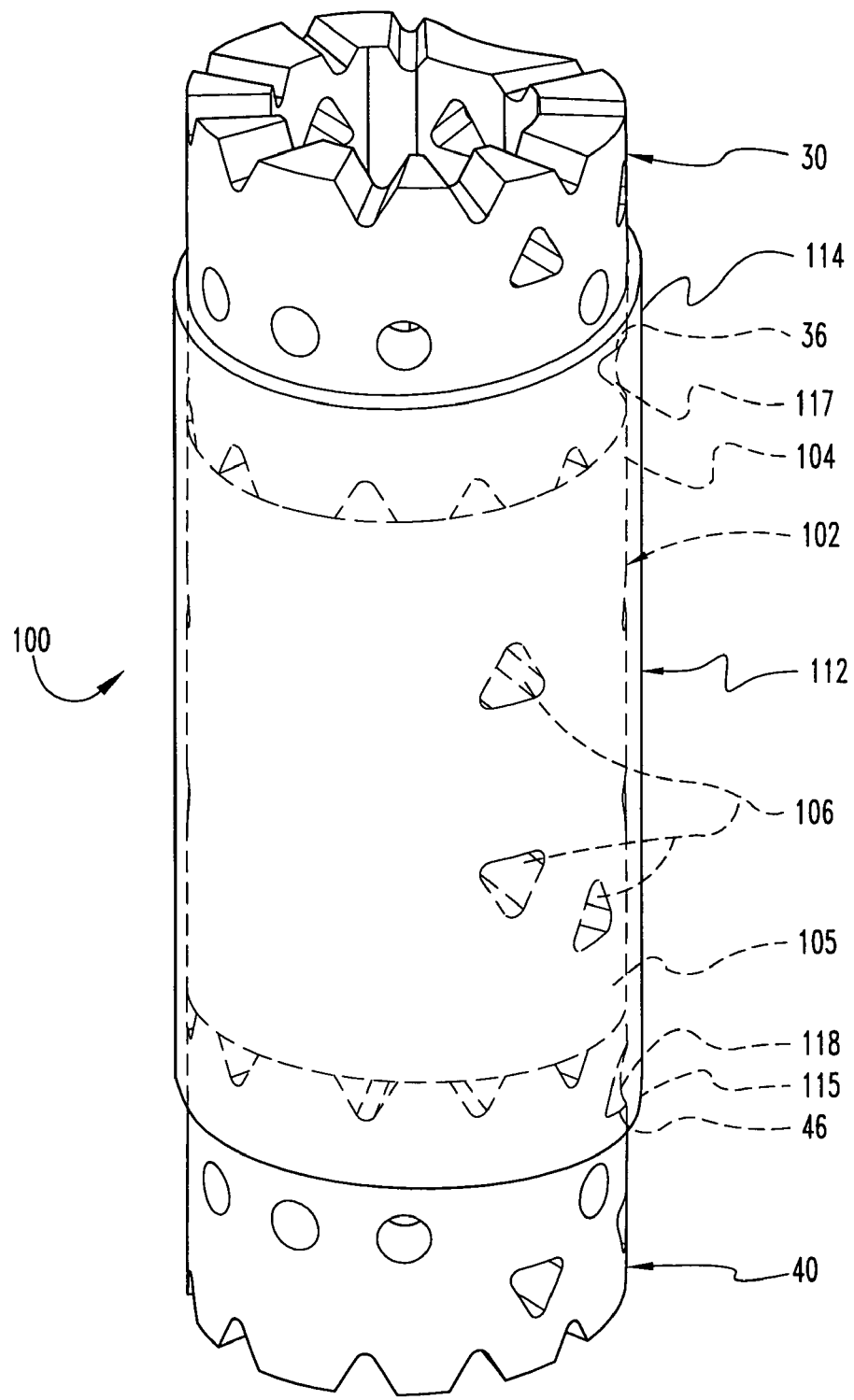
FIG. 10 is a perspective view of another embodiment vertebral replacement device.

In FIG. 10 there is provided an alternate embodiment vertebral replacement device 100. Device 100 includes upper member 30 and lower member 40 engaged at opposite ends of a vertebral body or connecting member 102, which can be similar to connecting member 12 discussed above. Connecting member 102 does not include upper and lower extensions extending from ends 104 and 105. To secure upper member 30 and lower member 40 to connecting member 102, a sleeve 112 is provided around connecting member 102 that has an upper end 114 overlapping upper member 30 and a lower end 115 overlapping lower member 40.

Sleeve 112 can be provided with engaging members 117, 118 in the form of projections, engaging members, tabs or the like on its inner wall surface. Engaging members 117, 118 engage apertures 36, 46 or other receptacle or detent in the outer wall surfaces of upper member 30 and lower member 40, respectively. Engaging members could also be provided to engage apertures 106 or other receptacle or detent in connecting member 102. So engaged, sleeve 112 resists axial movement of upper member 30 and lower member 40 relative to connecting member 102.

It is further contemplated that rotation of upper member 30 and lower member 40 relative to connecting member 102 could be prevented by a non-circular, telescoping interface between the members such as discussed above. In another embodiment, rotation of upper member 30 and lower member 40 relative to connecting member 102 could be prevented by the engagement of sleeve 112 with the upper and lower members 30, 40 and, if so configured, with connecting member 102. In yet a further form of the embodiment of FIG. 10, the connecting member 102 could be integral with sleeve member 112 to provide upper and lower bearing surfaces within sleeve 112 for support of upper member 30 and lower member 40 thereon.

Figure 11:
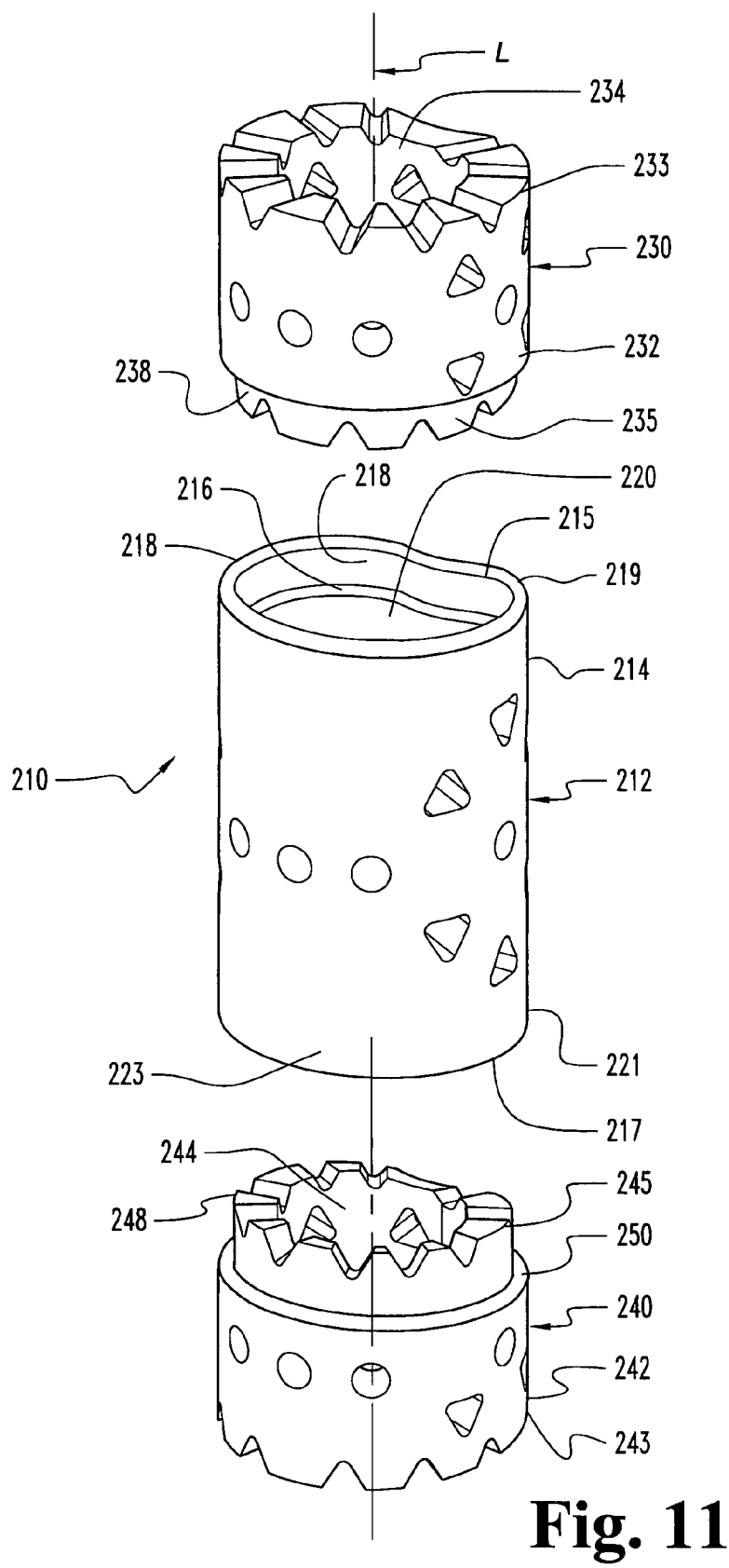
FIG. 11 is an exploded perspective view of another embodiment vertebral replacement device.

Referring now to FIG. 11, another embodiment vertebral replacement device 210 is shown. Device 210 includes a vertebral replacement or connecting member 212 having a body 214 extending between an upper end 219 and a lower end 221. Upper end 219 includes an upper extension 218 having an end surface 215 therearound. Extension 218 extends around a bearing surface 216 at the upper end of chamber 220. Bearing surface 216 is positioned below end surface 215 in chamber 220. Second end 217 similarly includes an extension 223 having an end surface 217, and a bearing surface (not shown) at the lower end of chamber 220 below end surface 217.

A first disc replacement or upper member 230 includes a body 232 having an upper end 233 and a lower end 235. Body 232 extends around a chamber 234. A second disc replacement or lower member 240 includes a body 242 having a lower end 243 and an upper end 245. Body 242 extends around a chamber 244. Lower member 240 includes an inset wall 248 extending around chamber 244, and a bearing surface 250 extending around body 242 below inset wall 248. Upper member 230 similarly includes an inset wall 238 and a bearing surface (not shown) extending around body 232 above inset wall 238.

When assembled, inset wall 238 of upper member 230 is received in chamber 220 of connecting member 212 with extension 218 extending around inset wall 238. Similarly, inset wall 248 of lower member 240 is received in chamber 220 of connecting member 212 with extension 223 extending around inset wall 248. It contemplated that end surface 215 can contact the bearing surface extending around inset wall 238, and that end surface 217 can contact bearing surface 250 extending around inset wall 248. Additionally or alternatively, the lower end of inset wall 238 can contact bearing surface 216 in chamber 220 at the upper end of connecting member 212, and the upper end of inset wall 248 can contact the bearing surface (not shown) in chamber 220 at the lower end of connecting member 212.

Connecting member 212 and/or upper and lower members 230, 240 could be provided with engaging members or a sleeve such as discussed above to prevent axial and/or rotational movement of upper and lower members 230, 240 relative to connecting member 212 when device 210 is assembled. In a further embodiment, connecting member 212 does not include the upper bearing surface 216 and the lower bearing surface in chamber 220 since extensions 218, 223 are not provided on connecting member 212. In this embodiment, inset walls 238 and 248 are received in chamber 220 at the respective end of connecting member 212, and end surfaces 215, 217 contact respective ones of the bearing surfaces extending around inset walls 238, 248.

Figure 12:
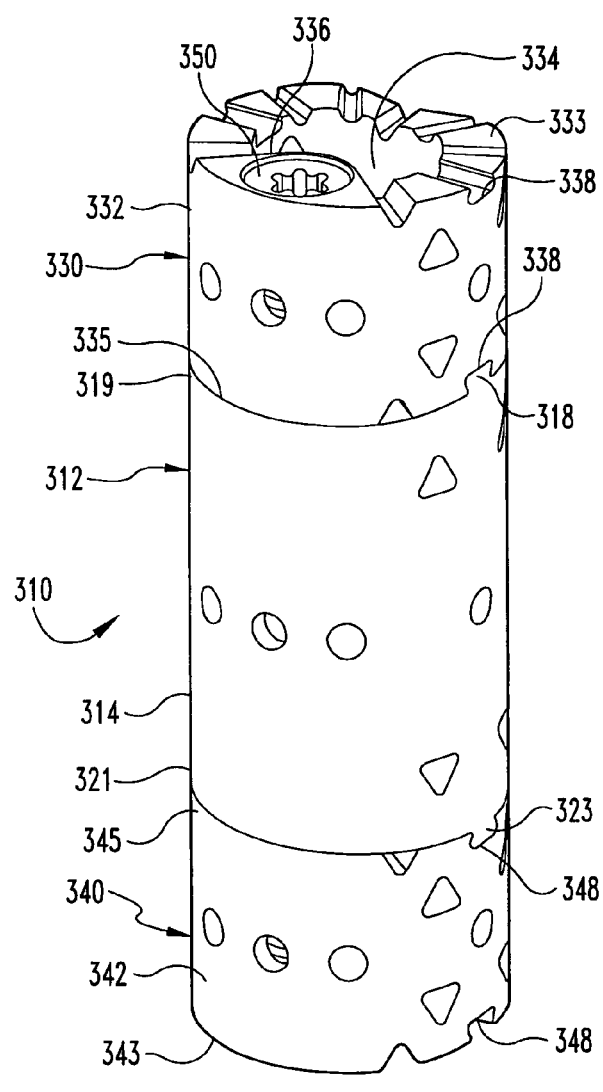
FIG. 12 is a perspective view of a vertebral replacement device according to another embodiment.
Figure 13:
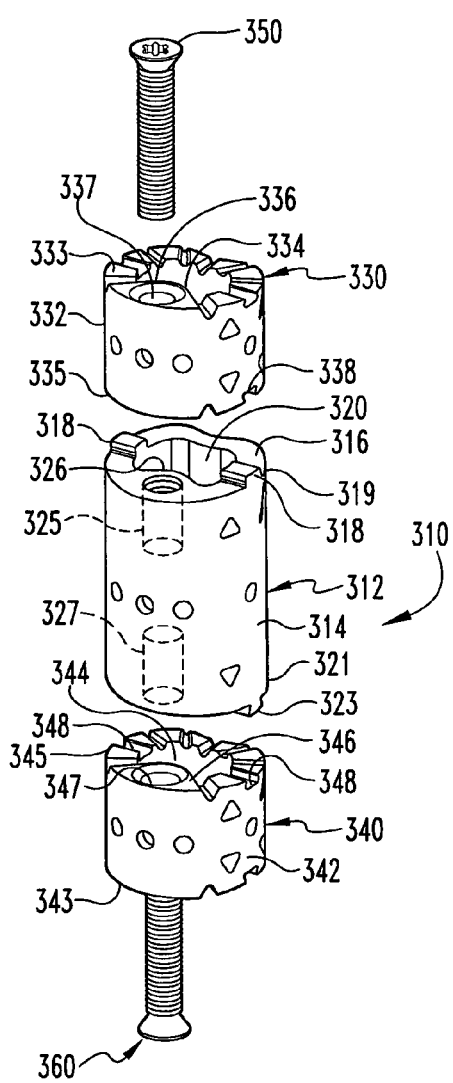
FIG. 13 is an exploded perspective view of the vertebral replacement device of FIG. 12.

Referring now to FIGS. 12 and 13, another embodiment vertebral replacement device 310 is shown. Device 310 includes a vertebral replacement or connecting member 312 having a body 314 extending between an upper end 319 and a lower end 321. Upper end 319 includes a pair of upper extensions 318 extending from a bearing surface 316 at the upper end of chamber 320. Lower end 321 similarly includes extensions 323 and a bearing surface (not shown) at the lower end of chamber 320.

A first disc replacement or upper member 330 includes a body 332 having an upper end 333 and a lower end 335. Body 332 extends around a chamber 334. A second disc replacement or lower member 340 includes a body 342 having a lower end 343 and an upper end 345. Body 342 extends around a chamber 344. Lower member 340 includes receptacles 348 sized and shaped to slidingly receive respective ones of the extensions 323 therein. Similarly, upper member 330 includes receptacles 338 formed in lowed end 335 sized and shaped to slidingly receive extensions 318 therein. Receptacles 338, 348 can be provided at each end of members 330, 340 so that either end can be secured to connecting member 312.

It is contemplated that extensions 318, 323 can include an enlarged outer end that provides a trapezoidal shape so that when positioned in the correspondingly shaped receptacle 338, 348 in dovetail fashion vertical displacement of members 330, 340 relative to connecting member 312 is resisted. Accordingly, upper and lower members 330, 340 are positioned on connecting member 312 by laterally sliding the upper and lower members 330, 340 onto extensions 318, 323. Other shapes for extensions 318, 323 and receptacles 338, 348 are also contemplated, including hook-shaped, triangular shaped, or other irregular shape that provides vertical securement. Extensions 318, 323 also resist rotation of the members 330, 340 relative to connecting member 312.

In order to prevent lateral displacement of upper member 330 in the direction between extensions 318 and also to provide further vertical engagement, an upper coupling member 350 is provided to secure upper member 330 to connecting member 312. Similarly, a lower coupling member 360 is provided to secure lower member 340 to connecting member 312. Upper member 330 includes a wall portion 336 that is enlarged and provided with a through-hole 337. Upper coupling member 350 is positionable in hole 337 to engage connecting member 312, vertically and laterally securing upper member 330 thereto. Similarly, lower member 340 includes a wall portion 346 that is enlarged and provided with a through-hole 347. Lower coupling member 360 is positionable in hole 347 to engage connecting member 312, vertically and laterally securing lower member 340 thereto.

Coupling members 350, 360 can be provided in the form of screws that threading engage respective ones of the passages 325, 327 extending into connecting member 312. Passages 325, 327 can be formed in an enlarged wall portion 326 of connecting member 312. In one embodiment, passages 325, 327 include a blind end and do not extend through connecting member 312. It is contemplated that passages 325, 327 can be threaded to threadingly engage coupling members 350, 360. Holes 337, 347 can be threaded or non-threaded. Other embodiments contemplate that passages 325, 327 form a single continuous passage through connecting member 312. It is further contemplated that wall portions 326, 336, 346 need not be enlarged relative to the remaining portion of the wall of the members 312, 330, 340, but rather can form part of a wall of uniform thickness. In addition, bearing surfaces 316, 321 include a smooth surface profile thereabout, although other surface profiles are also contemplated. The upper and lower bearing surfaces of members 330, 340 can be configured as discussed above with respect to members 30, 40.

Figures 14, 15:
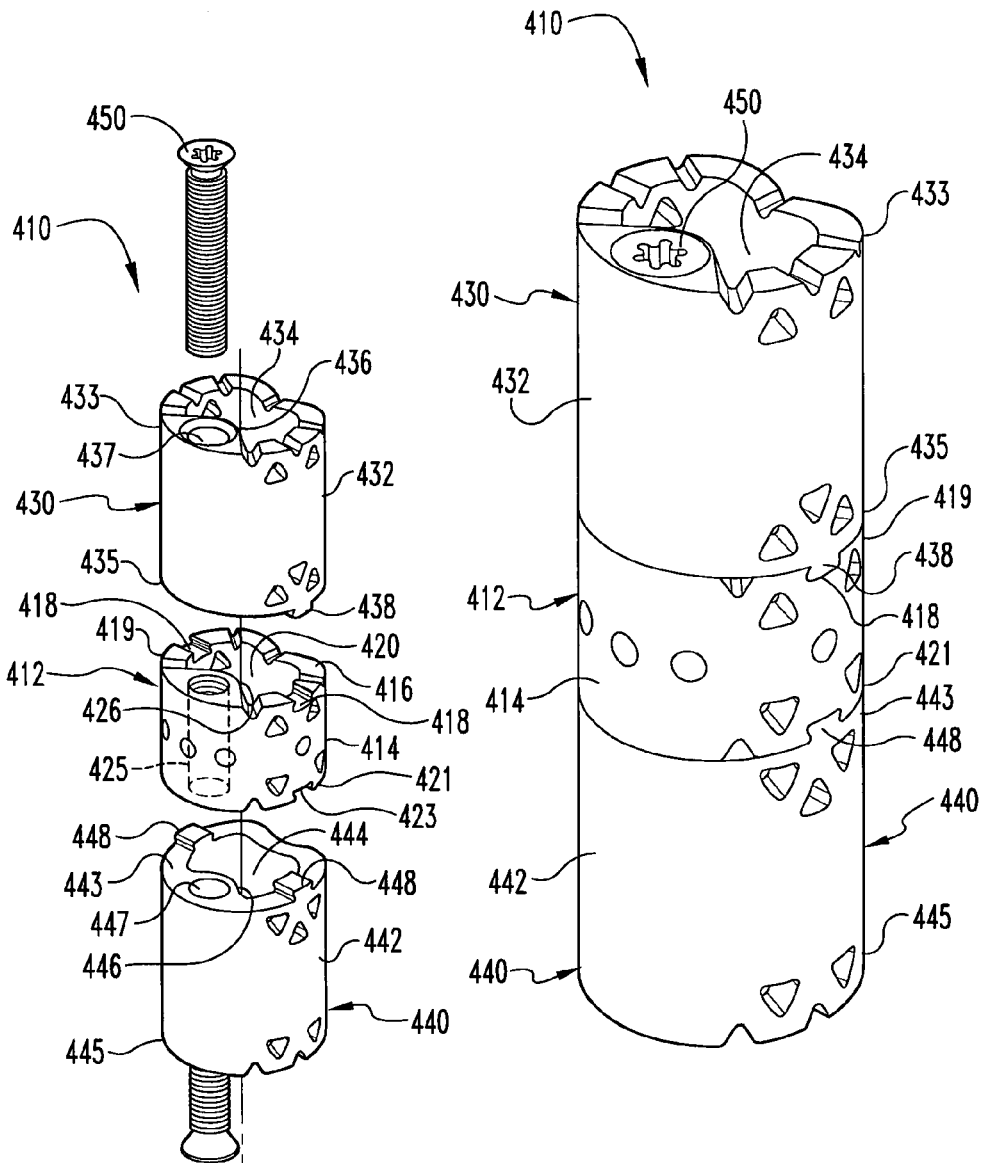
FIG. 14 is a perspective view of a vertebral replacement device according to another embodiment.
FIG. 15 is an exploded perspective view of the vertebral replacement device of FIG. 14.

Referring now to FIGS. 14 and 15, another embodiment vertebral replacement device 410 is shown. Device 410 includes a disc replacement or connecting member 412 having a body 414 extending between an upper end 419 and a lower end 421. Upper end 419 includes a pair of upper receptacles 418 extending into a bearing surface 416 at the upper end of chamber 420. Lower end 421 similarly includes receptacles 423 and a bearing surface (not shown) at the lower end of chamber 420.

A first vertebral body or upper member 430 includes a body 432 having an upper end 433 and a lower end 435. Body 432 extends around a chamber 434. A second vertebral body or lower member 440 includes a body 442 having a lower end 443 and an upper end 445. Body 442 extends around a chamber 444. Lower member 440 includes extensions 448 sized and shaped for sliding receipt in respective ones of the receptacles 423. Similarly, upper member 430 includes extensions 438 extending from lower end 435 thereof sized and shaped for sliding receipt in receptacles 418 of connecting member 412. It is contemplated that extensions 438, 448 can be configured as discussed above with respect to vertebral replacement device 310. Extensions 438, 448 can be omitted from upper end 433 of upper member 430 and lower end 445 of lower member 440 to provide sufficient bearing surface area at each end for contact with an adjacent vertebral endplate.

Coupling members 450, 460 prevent lateral displacement and also provide vertical engagement as discussed above with respect to coupling members 350, 360. Accordingly, upper member 430 includes a wall portion 436 that is provided with a through-hole 437. Upper coupling member 450 is positionable in hole 437 to engage connecting member 412, vertically and laterally securing upper member 430 thereto. Similarly, lower member 440 includes a wall portion 446 that is provided with a through-hole 447. Lower coupling member 460 is positionable in hole 447 to engage connecting member 412, vertically and laterally securing lower member 440 thereto.

Coupling members 450, 460 can be provided in the form of screws that threadingly engage passages 425 extending through connecting member 412. Passage 425 can be formed in wall portion 426 of connecting member 412. In one embodiment, passage 425 can be separated into separate portions with blind ends so that passage 425 does not extend through connecting member 412.

In the embodiment of FIGS. 14 and 15, connecting member 412 is provided with a height between ends 419, 421 that approximates the height of a vertebral disc space. Accordingly, connecting member 412 can be used in an unstacked configuration as a disc space replacement member. Bearing surfaces 416 at ends of connecting member 412 can be configured to engage the vertebral endplates, such as discussed above with respect to device 10 and upper and lower members 30, 40. It is also contemplated that connecting member 412 can be used with only one of the upper and lower members 430, 440. Upper and lower members 430, 440 can be provided with a height that allows the assembled vertebral replacement device 410 to replace one or more vertebral bodies and one or more disc spaces removed from a portion of the spinal column.

Figures 16, 17:
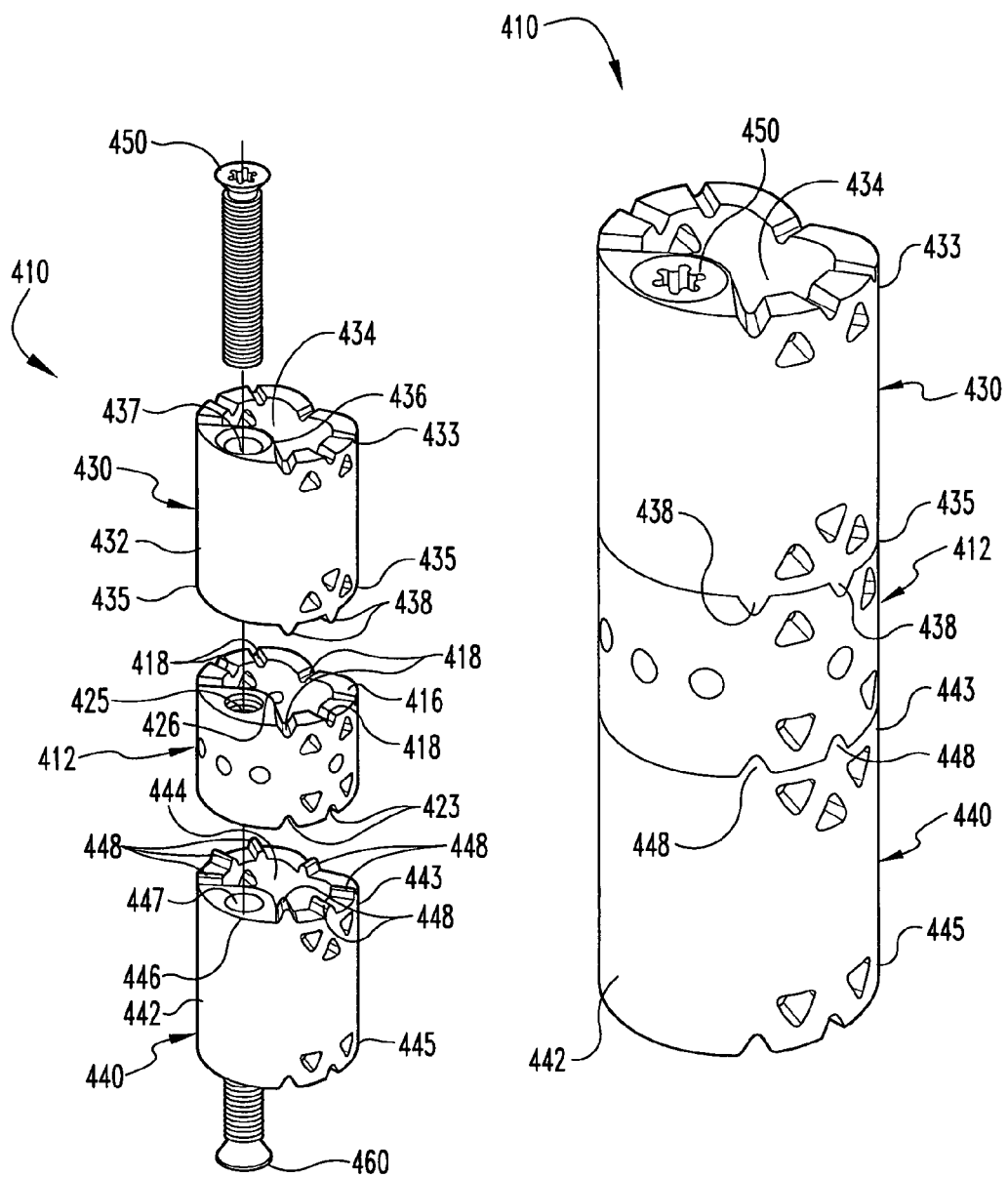
FIG. 16 is a perspective view of a vertebral replacement device according to another embodiment.
FIG. 17 is an exploded perspective view of the vertebral replacement device of FIG. 16.

Referring now to FIGS. 16 and 17, another embodiment for vertebral replacement device 410 is shown with another embodiment engagement arrangement between connecting member 412 and members 430,440. In this embodiment, upper member 430 is provided with a number of extensions 438 and lower member 440 is provided with a number of extensions 448. Extensions 438 are positionable in receptacles 418 formed in upper bearing surface 416 of connecting member 412. Extensions 448 can be positioned in corresponding receptacles 423 formed in the lower bearing surface of connecting member 412. Extensions 438, 448 and receptacles 418, 423 are configured so that members 430, 440 can be end-loaded onto connecting member 412, and thus do not resist displacement of members 430, 440 away from connecting member 412. Extensions 438, 448 are radially dispersed about the center of members 430, 440 to provide torsional and lateral stability for members 430, 440 when positioned in the correspondingly positioned receptacles 418, 423 of connecting member 412. Coupling members 450, 460 provide axial stability for the assembled device 410.

Figure 18:
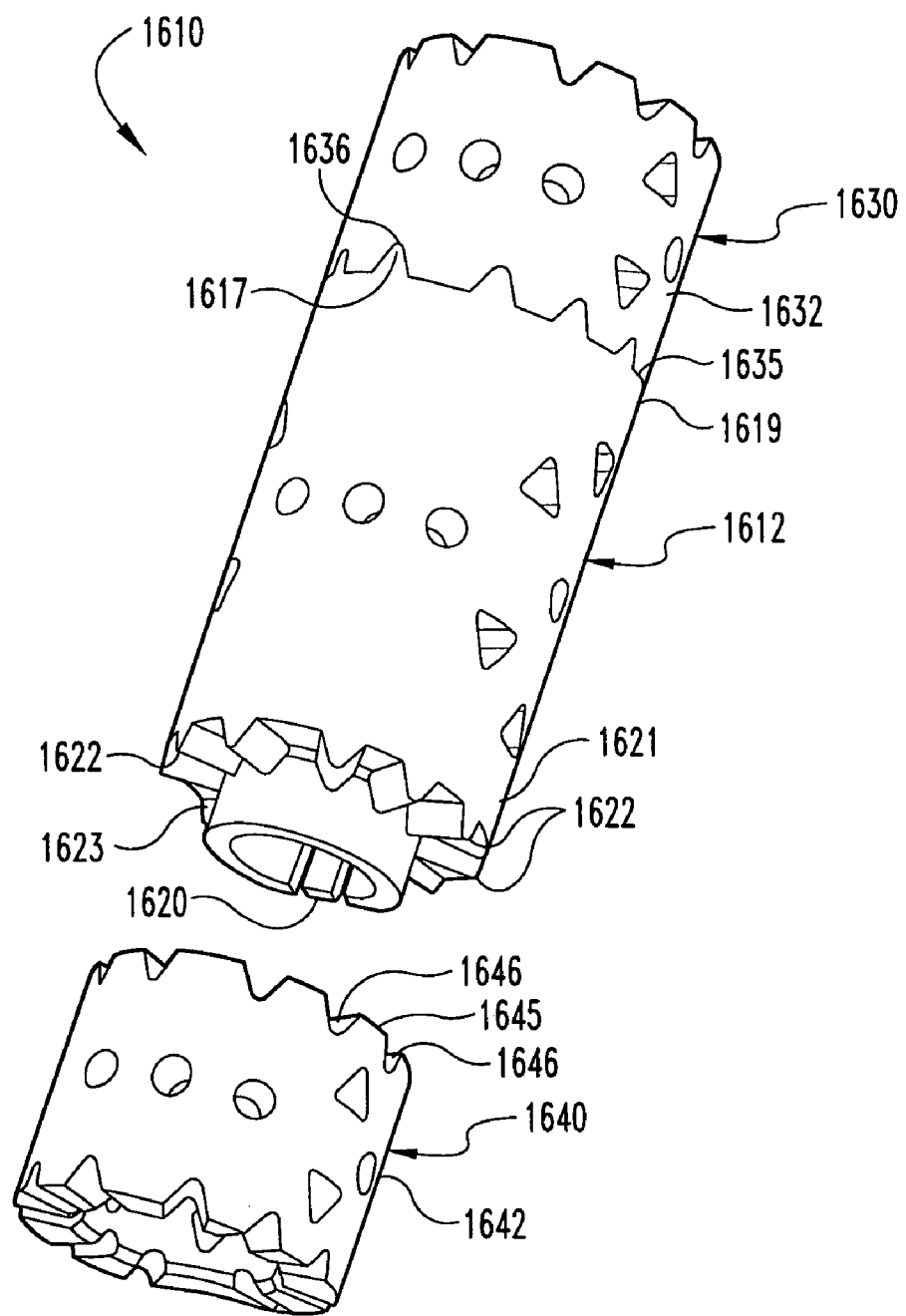
FIG. 18 is a partially exploded perspective view of a vertebral replacement device according to another embodiment.

Referring to FIG. 18 there is shown vertebral replacement device 1610 including a connecting member 1612, an upper member 1630 and a lower member 1640. Connecting member 1612 includes an upper end 1619 having a number of projections radially spaced about an upper bearing surface thereof. Connecting member 1612 includes a lower end 1621 including a number of projections 1622 radially spaced about a lower bearing surface thereof. As discussed above with respect to vertebral replacement device 10, connecting member 1612 can include extensions at the upper and lower ends thereof such as shown with extension 1623, to telescopically receive the adjacent upper and lower members 1630, 1640. An engaging member 1620 at each of the upper and lower extensions includes an engaging portion that engages the adjacent upper and lower member 1630, 1640 to axially secure the adjacent upper and lower members 1630, 1640 to connecting member 1612.

Each of the upper and lower members 1630, 1640 include radially spaced recesses 1636, 1646 formed in lower surface 1635 of body 1632 and upper surface 1645 of body 1642, respectively. Recesses 1636, 1646 are sized and shaped to receive corresponding ones of the projections 1617, 1622 when device 1610 is assembled. Recesses 1636, 1646 also extend along a radius extending from the center of the corresponding upper and lower member 1630, 1640 in order to receive the respective projections 1617, 1622. The radial interdigitation of the radially spaced projections and recesses provides resistance to displacement of the members 1630, 1640 relative to connecting member 1612 as a result of torsional loading. Further, the radial spacing of the projections universally about the center axis of device 10 provides resistance to displacement of the members 1630, 1640 relative to connecting member 1612 as a result of lateral loading applied from any direction. In the illustrated embodiment, projections 1617, 1622 are V-shaped, and the peak of the v-shape extends along a radius extending from the center of connecting member 1612.

Figure 19:
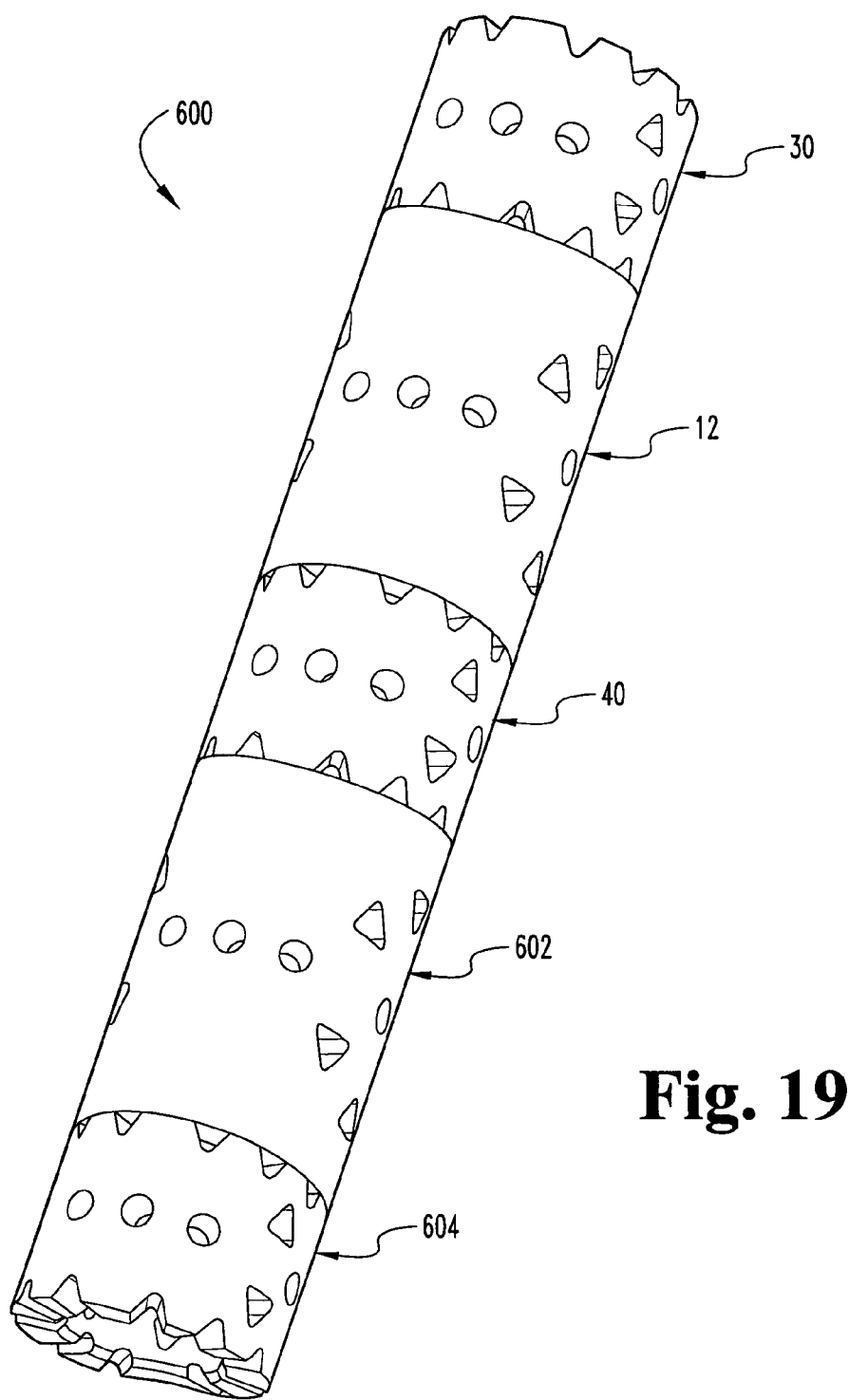
FIG. 19 is a perspective view of a vertebral replacement device according to another embodiment.

As shown in FIG. 19, the vertebral replacement devices can include modular components or members so that more than three members can be stacked one upon the other to provide a vertebral replacement device of the desired overall height. For example, vertebral replacement device 600 includes an upper member 30, a connecting member 12, and a first lower member 40. Members 12, 30 and 40 are illustrated as including a configuration as discussed above with respect vertebral replacement device 10, or can include any configuration discussed herein. A second connecting member 602, which can be identical to connecting member 12, can be coupled to the lower end of first lower member 40. A second member 604, which can be identical to upper and/or lower members 30, 40, is coupled to the lower end of connecting member 602. Accordingly, any number of components can be stacked one upon another and axially secured as discussed herein to provide a vertebral replacement device of desired overall height.

In the embodiment illustrated in FIG. 19, connecting members 12, 602 can each be provided with a height that approximates the height of a vertebral body. Upper and lower members 30, 40, 604 can approximate the height of a spinal disc space. Thus, vertebral replacement device 600 can be employed in a corpectomy procedure in which a pair of vertebrae are removed along with the spinal disc spaces between the remaining intact vertebrae.

Figure 20:
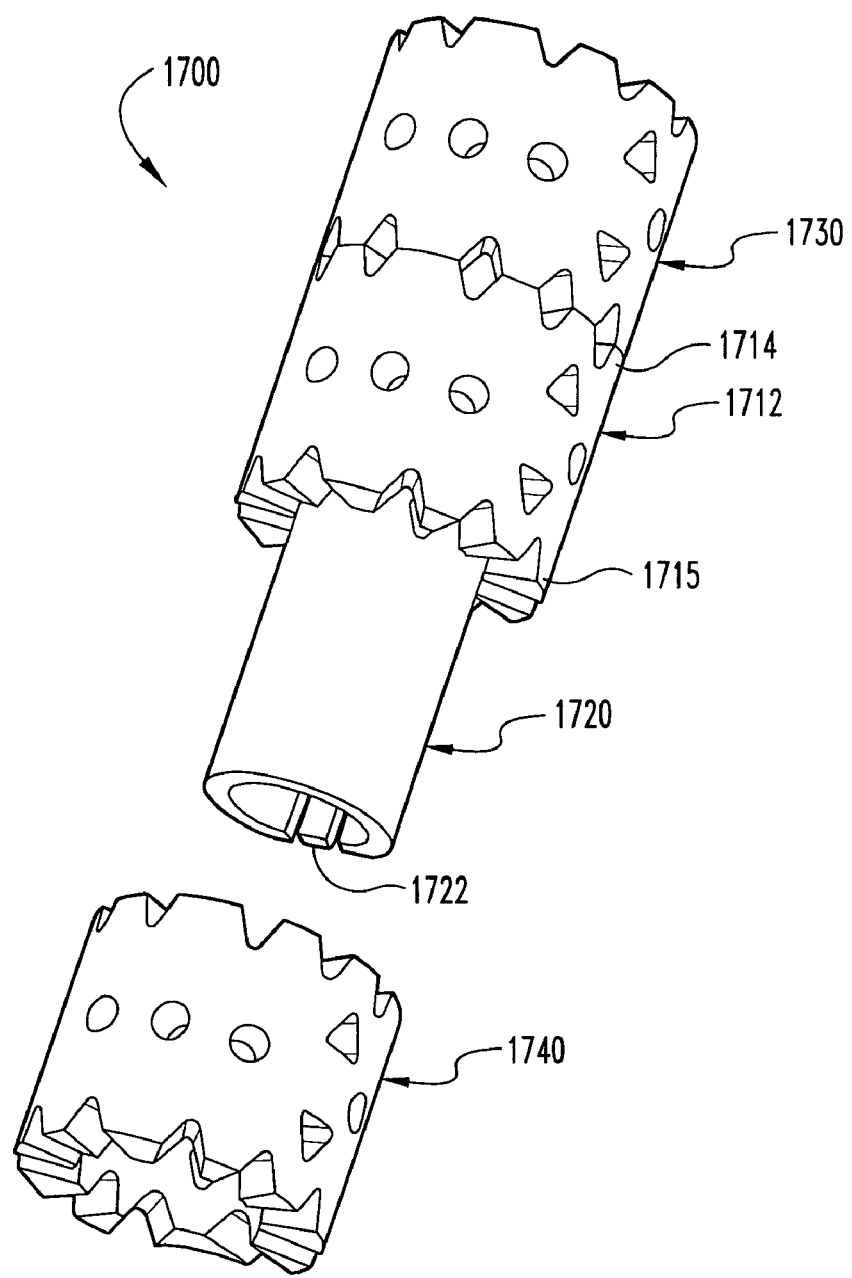
FIG. 20 is a partially exploded perspective view of a vertebral replacement device according to another embodiment.

Referring now to FIG. 20, another embodiment vertebral replacement device 1700 includes a first disc replacement or upper member 1730 and second disc replacement or lower member 1740 engaged at opposite ends of a vertebral body or connecting member 1712. Connecting member 1712 can be identical to upper and lower members 1730, 1740. In the illustrated embodiment, connecting member 1712 does not include upper and lower extensions or engagement members extending from ends 1714 and 1715. Ends 1714, 1715 are adapted to bearing against the endplates of adjacent vertebrae when connecting member 1712 is positioned in isolation in the disc space between vertebrae.

Connecting member 1712 can be employed in a vertebral replacement device 1700 by securing at least one of the members 1730, 1740 at one end thereof. A sleeve 1720 is provided that is positionable in the chambers of connecting member 1712, upper member 1730 and lower member 1740 and slidable relative thereto. Sleeve 1720 includes an engaging member 1722 formed in its wall at the opposite ends thereof. Engaging member 1720 can be configured as discussed above with respect to engaging member 20 discussed above. Engaging member 1722 can include an engaging portion that includes a lateral projection or the like to resiliently engage an opening in the inner wall surface of upper and lower members 1730, 1740 to axially secure upper and lower members 1730, 1740 thereto with connecting member 1712 therebetween.

Connecting member 1712 and/or one or both of the members 1730, 1740 can he provided with a height adapted to replace a vertebral body. Sleeve 1720 can include a length between its opposite ends adapted to secure two, three or four or more members to one another axially. Sleeve 1720 can also include a non-circular cross-section that non-rotatably and slidingly accepts a similarly shaped non-circular chamber of the members 1712, 1730, 1740. Sleeve 1720 can be provided with a hollow interior opening at each end to permit fusion therethrough. It is further contemplated that sleeve 1720 can be solid and comprise a bone graft or other suitable bone replacement material. Sleeve 1720 could also be a solid body with a number of holes formed therethough to permit fusion.

Figure 21:
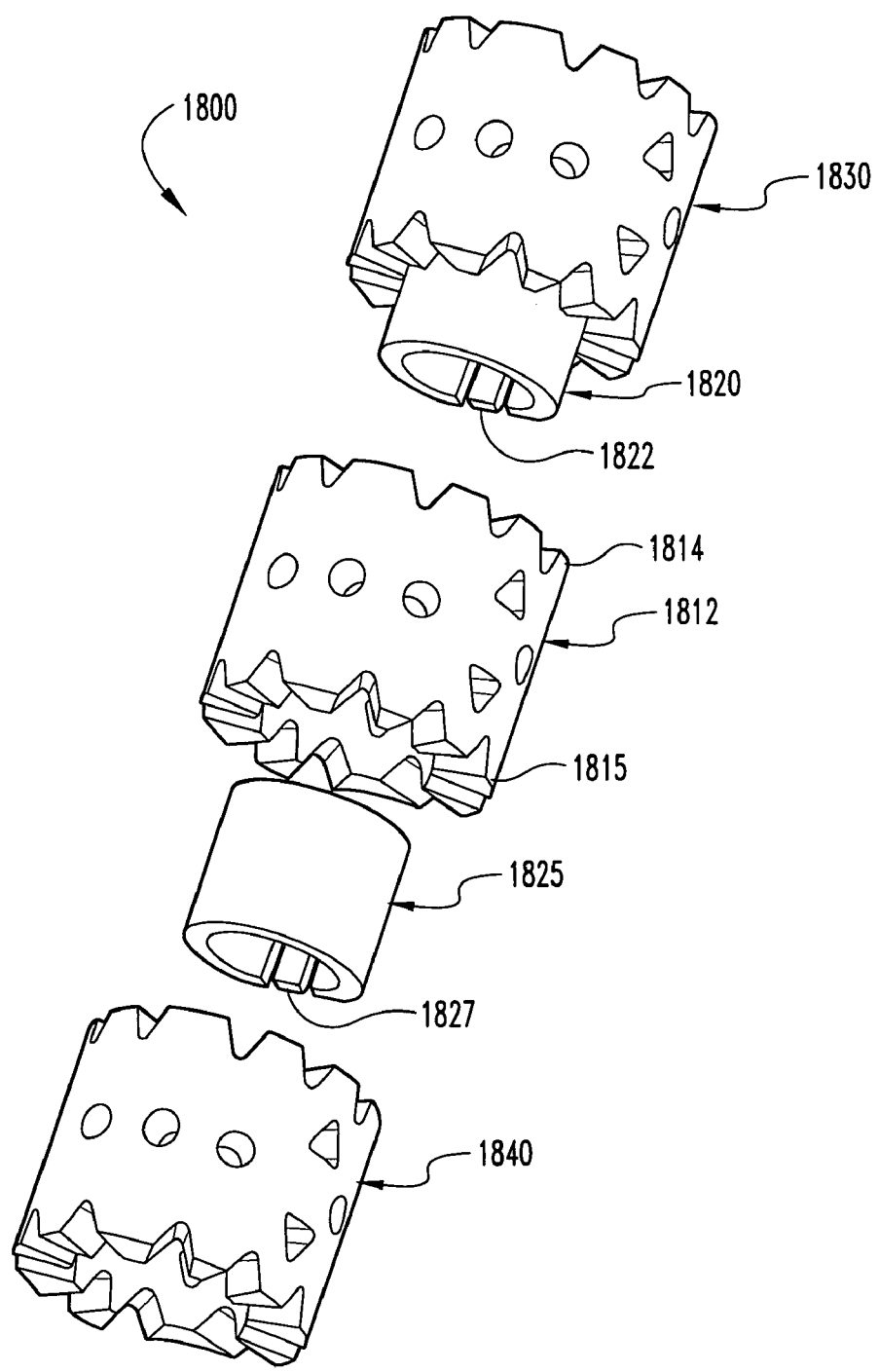
FIG. 21 is an exploded perspective view of a vertebral replacement device according to another embodiment.

Referring to FIG. 21, another embodiment vertebral replacement device 1800 includes a first disc replacement or upper member 1830 and second disc replacement or lower member 1840 engaged at opposite ends of a vertebral body or connecting member 1812. Connecting member 1812 can be identical in size and shape to upper and lower members 1830, 1840 as illustrated, or can be different in size and shape. Members 1812, 1830, 1840 can be employed when unstacked in disc space replacement procedures or in corpectomy procedures when stacked.

To secure upper member 1830 and lower member 1840 to connecting member 1812, a first sleeve 1820 is provided that is positionable in the chambers of connecting member 1812 and upper member 1830, and a second sleeve 1825 is provided that is positionable in the chambers of connecting member 1812 and lower member 1840.

Sleeves 1820, 1825 include each include engaging members formed in the wall thereof at opposite ends thereof. For example, engaging member 1822 is shown at the lower end of sleeve 1820, and engaging member 1827 is shown at the lower end of sleeve 1825. The engaging members at the upper ends of sleeves 1820, 1822 are not shown. The engaging members can be provided as discussed above with respect to engaging member 20. Engaging members 1822, 1827 can include an engaging portion that includes a lateral projection or the like that engages an opening in the inner wall surface of connecting member 1812 and the adjacent upper and lower members 1830, 1840 to axially secure upper and lower members 1830, 1840 thereto.

Sleeves 1820, 1825 can include a length to secure two members to one another axially. An additional sleeve can be provided for each additional member to be added to the end of upper and/or lower members 1830, 1840. A two member stack can be formed with a single sleeve 1820, 1825. Sleeves 1820, 1825 can also include a non-circular cross-section that non-rotatably and slidingly accepts a similarly shaped non-circular chamber of the members 1812, 1830, 1840. Sleeves 1820, 1825 can be provided with a hollow interior opening at each end to permit fusion therethrough. It is further contemplated that sleeves 1820, 1825 can be solid and comprise a bone graft or other suitable bone replacement material. Sleeves 1820, 1825 could also be a solid body with a number of holes formed therethough to permit fusion.

FIGS. 22 and 23 illustrate another embodiment for the upper and lower disc replacement members that comprise the vertebral replacement devices discussed herein. Disc replacement member 1900 can be coupled to the upper or lower end of a connecting member, such as connecting member 12 discussed above, or received over the end of a sleeve, such as sleeves 1720, 1820 discussed above. Disc replacement member 1900 includes a side wall 1910 extending between a first end 1902 and an opposite second end 1904. First end 1902 includes an opening in communication with chamber 1906. Second end 1904 includes an upper wall 1908 having a plurality of openings 1912 in communication with chamber 1906.

Side wall 1910 includes a number of openings 1916 in communication with chamber 1906. Openings 1916 can be circular, triangular, or include any other suitable configuration. One or more of the openings 1916 can be adapted to engage an insertion instrument. First end 1902 includes a bearing surface 1914 extending about chamber 1906 to bear against a support surface of a connecting member, or against the endplate of an adjacent vertebra. Upper wall 1908 forms an upper surface adapted to bear against the endplate of an adjacent vertebra. Upper wall 1908 can be flat, or provided with a convex curvature adapted to fit with the concave curvature of an adjacent vertebral endplate. In the illustrated embodiment, upper wall 1908 and bearing surface 1914 define a kidney-shape, although other shapes are also contemplated, including circular, oval, square, rectangular, polygonal, and any other non-circular shape.

Referring now to FIGS. 24-26, there is shown another embodiment vertebral replacement device 510. Each of the vertebral replacement devices 510 is generally identical, and includes a connecting member 512, an upper member 530 and a lower member 540. However, the devices include overall heights that vary from one to the other, and each of the devices includes members having heights that vary from one to the other. For example, device 510 in FIG. 24 includes an overall height 580 formed by members 512, 530, 540, each of which have approximately the same height 581. Height 581 can be adapted for each of the members 512, 530, 540 to be used in a spinal disc space in an unstacked arrangement for interbody fusion.

Vertebral replacement device 510 in FIG. 25 includes an overall height 582 adapted for corpectomy procedures in which a vertebral body and associated spinal discs have been removed. In FIG. 25, upper and lower members 530, 540 each include a height 583, and connecting member 512 includes a height 584. Height 583 is greater than height 584. Vertebral replacement device 510 in FIG. 26 includes an overall height 586 adapted for corpectomy procedures in which a vertebral body and associated spinal discs have been removed. In FIG. 26, upper and lower members 530, 540 each include a height 587 that is greater than height 583 and height 584. Thus, when unstacked, the various heights provided by members 512, 530, 540 provide the surgeon a range of heights from which to select a disc space replacement member for an interbody fusion procedure. It is further contemplated members of various heights 582, 583, 584, and 587 can be provided in a kit, and the surgeon can mix and match selected members and secure the selected members to one another to provide a vertebral replacement device of overall height sized to provide the desired fit in the space left by one or more removed vertebrae.

For each of the embodiments in FIGS. 24-26, connecting member 512 includes a body 514 extending between an upper end 519 and a lower end 521. Upper member 530 includes a body 532 extending between and upper end 533 and a lower end 535. Body 532 defines a chamber 534 extending between and opening at upper end 533 and lower end 535. Lower member 540 includes a body 542 extending between and upper end 543 and a lower end 545. Body 542 defines a chamber 544 extending between and opening at upper end 543 and lower end 545. Connecting member 512 can be provided with a chamber (not shown) extending between upper end 519 and lower end 521 in communication with chambers 534, 544.

Connecting member 512 include a number of elongated ridges 523 extending along its upper end surface adjacent upper end 519, and a number of elongated ridges 525 along the end surface adjacent lower end 521. Upper member 530 includes a number of elongated ridges 531 along its upper surface adjacent upper end 532, and a number of elongated ridges 539 extending along its end surface adjacent lower end 535. Similarly, lower member 540 includes a number of elongated ridges 541 along its lower surface adjacent lower end 545, and a number of ridges 549 extending along its upper surface adjacent upper end 543. Adjacent ones of the elongated ridges 523, 539 and ridges 525, 549 interdigitate when upper and lower members 530, 540 are stacked on connecting member 512 and resist movement of the members relative to one another transversely to the ridges.

To resist axial displacement and displacement of the members relative to one another in the direction of the ridges, coupling members 550, 560 extend through a hole extending through the wall of upper member 530 between ends 533, 535. Coupling members 550, 560 engage aligned passages in connecting member 512. Lower member 540 can be similarly secured with coupling members (not shown) that extend through holes in lower member 540 and into aligned passages of connecting member 512.

When assembled as a stack, vertebral replacement device 510 can be inserted in the space between vertebrae. Connecting member 512 can be provided with anterior openings 516 along a convexly curved wall portion of body 514 to facilitate attachment of an insertion instrument for insertion of device 510 in anterior approach to the disc space. Oblique openings 517 can be provided in body 514 to facilitate attachment of an instrument for inserting vertebral replacement device 510 in an anterior oblique approach. Lateral openings 518 in the side wall portions of body 532 facilitate attachment of an instrument for inserting vertebral replacement device 510 in a lateral approach. Openings 516, 517, 518 can be any one or combination of threaded, non-threaded, slotted or combinations thereof, or other suitable configuration, for attachment of an insertion instrument. It is further contemplated that upper and lower members 530, 540 can also be provided with similarly positioned anterior, oblique or lateral openings for attachment of an insertion instrument.

Various windows can be provided in the lateral walls of upper and lower members 530, 540 to facilitate bone growth and visualization of the interior of chambers 534, 544. For example, upper member 530 includes windows 537 extending through lateral wall portions of body 532 in communication with chamber 534. Similarly, lower member 547 includes windows 547 extending through the lateral wall portions of body 542 in communication with chamber 544.

Vertebral replacement devices 510 are illustrated with a D shape extending therealong. When implanted, the convexly curved wall portions of bodies 514, 532, 542 can be oriented anteriorly. The opposite posterior wall portion of bodies 514, 532, 542 is relatively flat and posteriorly oriented when implanted. The anterior portions of the bodies 532, 542 of upper and lower members 530, 540, and the anterior portion of body 514 of connecting member 512, each include a wall thickness that allows the openings for coupling members 550, 560 to be formed therethrough. The increased thickness wall portions also provide additional bearing surface area at the ends of device 510 to support the vertebrae.

Referring now to FIGS. 27A and 27B, various configurations for the ridges along the upper and lower surfaces of member 530 and connecting member 512 are shown. Lower member 540 can also be provided with ridge configuration. In the illustrated embodiment, upper member 530 includes ridges 531, 539 having a swept-back profile. For example, each ridge 531 includes a peak 591 formed at the intersection of a first wall 593 and a second wall 595. Second wall 595 is sloped to facilitate insertion in the direction of arrow 590, and first wall 593 is more vertically oriented so that ridges 531 bite into the adjacent endplate upon movement or attempted movement in the direction opposite arrow 590. Ridges 539 include a similar profile so that either surface of member 530 can contact the adjacent vertebral endplate.

The swept back profile of ridges 531, 539 also facilitates engagement between the stacked members 530, 512. In the illustrated embodiment, the upper and lower bearing surface of member 530 are angled relative to one another at angle 552, and the upper and lower surfaces of connecting member 512 are angled relative to one another at angle 554. When stacked upon one another, the device forms an overall angle 556 between the upper surface of member 530 and the lower surface of connecting member 512. In the illustrated embodiment, the reduced height wall portion of member 530 is positioned adjacent greater height wall portion of connecting member 512. Accordingly, the overall angle 556 of device 510 is less than the angles 554, 552. The more vertically oriented wall portions of the ridges bear against one another, providing resistance to the adjacent inclined surfaces sliding relative to one another.

In FIG. 27B, upper member 530 includes ridges 531 oriented having gradually sloped wall portions 595 oriented in a direction opposite that of the gradually sloped wall portions of lower ridges 539. The upper and lower bearing surfaces of member 530 are oriented at an angle 558, and the upper and lower bearing surfaces of member 512 are oriented at angle 554. The reduced height wall portions of members 530, 512 are positioned adjacent one another, forming overall angle 556 between the upper surface of member 530 and lower surface of members 512 that is greater than angle 554 and angle 558. By providing ridges 531, 539 with orientations in the opposite direction, upper member can be flipped over and stacked on connecting member 512 to provide a lesser overall angle 556. This reduces the number of members required in a kit to provide the surgeon a number of options in arranging the stacked members to provide the desired angulation between the upper and lower end surfaces.

Referring now to FIGS. 28-29, another embodiment vertebral replacement device 610 includes a connecting member 612, an upper member 630, and a lower member 640. Connecting member 612 includes an upper extension 618 and a lower extension 623 extending from upper and lower ends 619 and 621, respectively. Upper member 630 includes a bore 636 extending between the upper and lower surfaces thereof, and lower member 640 includes a bore 646 extending between upper and lower surfaces thereof. Upper extension 618 is positionable in bore 636 of upper member 630, and lower extension 623 is positionable in bore 646 of lower member 540. Openings 638, 648 extend through a wall of upper and lower members 630, 640 and communicate with bores 636, 646.

When assembled, coupling members 650, 660 extend through openings 638, 648, respectively, and engage the adjacent extension 618, 623 in bores 636, 646. In the illustrated embodiment, extensions 618, 623 are integral with connecting member 612. The coupling members resist axial displacement of upper and lower members 630, 640 away from connecting member 612. When stacked one upon the other, chamber 634 of upper member 630 and chamber 644 of lower member 640 align with chamber 614 of connecting member 612. The aligned chambers provide an avenue for bony fusion of the supported vertebrae.

Figure 30:
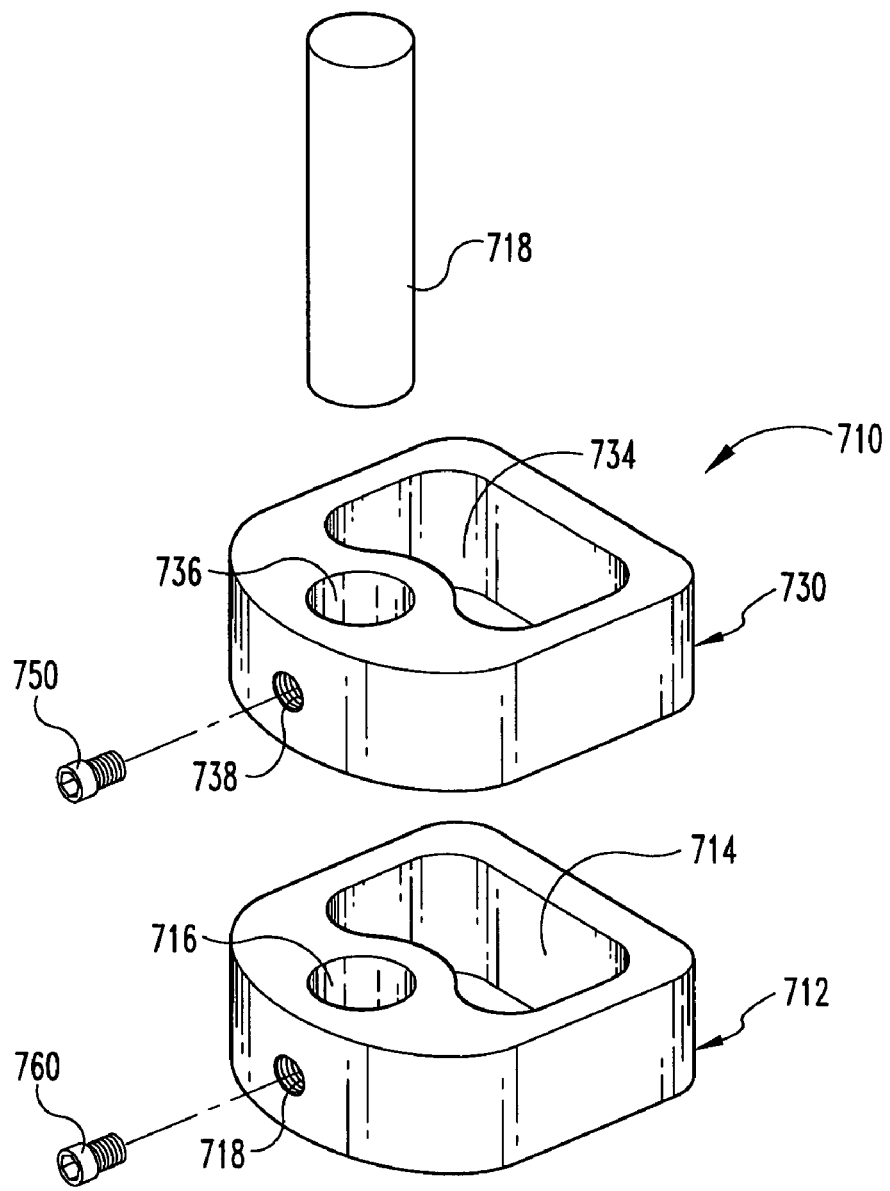
FIG. 30 is an exploded perspective view of another embodiment vertebral replacement device.

The adjacent surfaces of upper member 630 and connecting member 612, and the adjacent surfaces of connecting member 612 and lower member 640, can be provided with interdigitating ridges to resist lateral and rotational displacement. Extensions 618, 623 can also resist lateral displacement of the members relative to one another. Resistance to displacement from torsional forces can be provided by, for example, the interdigitating ridges on the adjacent faces of the stacked members as illustrated. Other embodiments contemplate that members 612, 630, 640 are provided without interdigitating ridges or surfaces. Additional coupling members or fasteners could be provided through the stacked members, or a non-rotatable, telescoping interface between members of the stack could be employed, to provide torsional, lateral and/or axial stability. In another embodiment, extensions 618, 623 can extend from one or both of the upper member 630 and lower member 640, and positioned in bores formed in connecting member 612 and secured thereto with coupling members. In FIG. 30, another embodiment vertebral replacement device 710 includes an upper member 730 and a lower or connecting member 712. Upper and lower members 712, 730 can include a D-shaped body with the convexly curved will anteriorly oriented between the adjacent vertebrae. Chambers 714, 734 are alignable when stacked to provide a passage for bony fusion. Other shapes and configurations for members 714, 734 are also contemplated as discussed herein.

An extension 718 is provided in the form of a rod that extends through bore 736 of upper member 730 and bore 716 of connecting member 712. Coupling members 750, 760 are positionable in openings 738, 718, respectively and engage extension 718 in bores 736, 716 to secure members 730, 712 thereto and to resist axial and lateral displacement of the members 730, 712 relative to one another. Members 712, 730 can be provided with interdigitating ridges, a non-rotatable telescoping interface, and/or other fasteners to secure members 712, 730 to one another. In another embodiment, extension 718 can include a non-circular cross-section, and is received in correspondingly shapes bores 716, 736 to resist rotational displacement of members 712, 730 relative to one another. In still another embodiment, extensions 718 can be provided with a length that allows three or more members to stacked and secured therealong.

Figure 31:
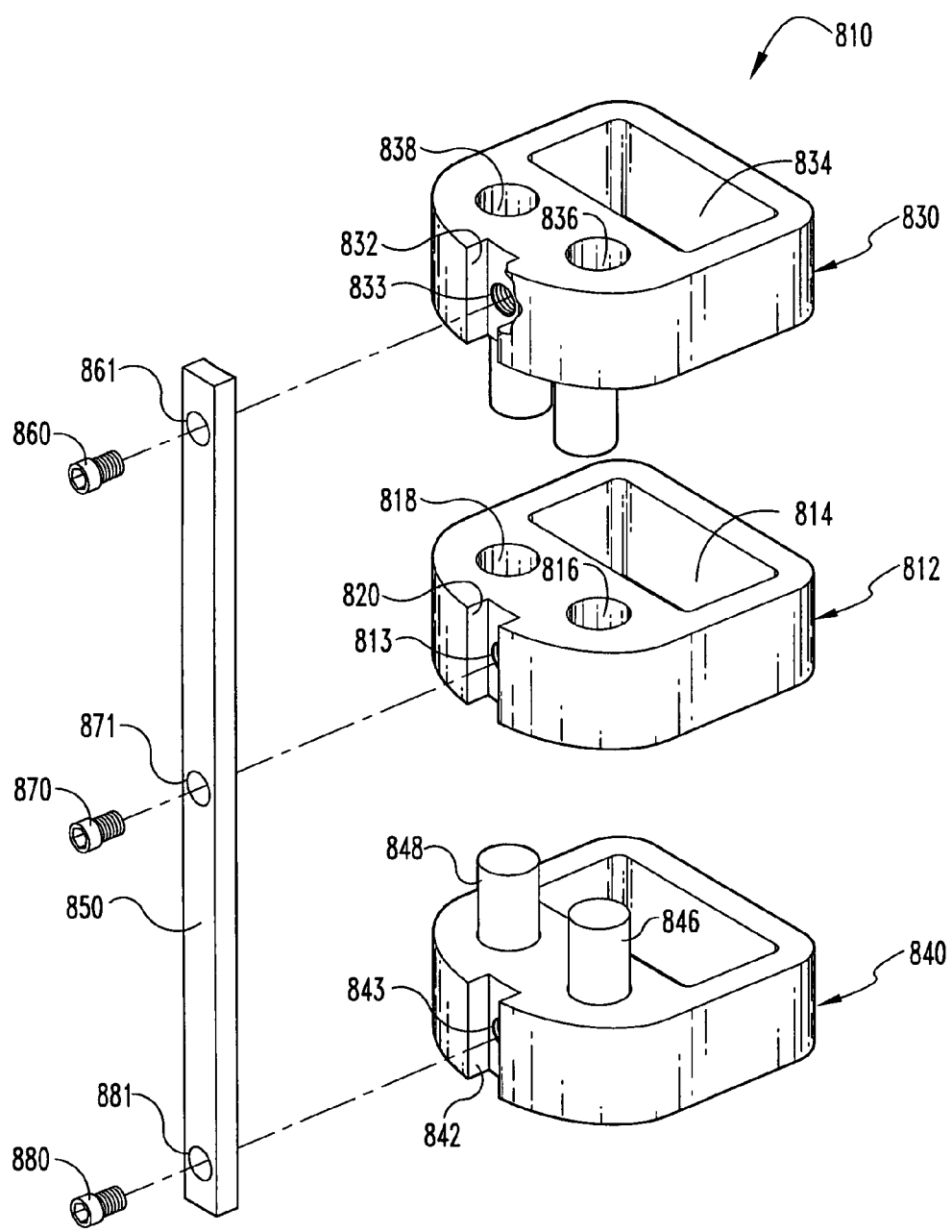
FIG. 31 is an exploded perspective view of another embodiment vertebral replacement device.

In FIG. 31, another embodiment vertebral replacement device 810 is shown with a connecting member 812 and upper and lower members 830, 840. Connecting member 812 and upper and lower members 830, 840 can include a D-shaped body with the convexly curved wall anteriorly oriented between the adjacent vertebrae. Chambers 814, 834, 844 are alignable when stacked to provide a passage for bony fusion. Other shapes and configurations for members 812, 830, 840 are also contemplated as discussed herein.

Connecting member 812 includes first and second passages 816, 818 extending between upper and lower bearing surfaces of connecting member 812. First and second passages 816, 818 are sized and shaped to receive first and second extensions 836, 838 of upper member 830 when upper member 830 is stacked thereon. The pair of extensions 836, 838 resist lateral and torsional movement of upper member 830 relative to connecting member 812. Similarly, lower member 840 includes first and second extensions 846, 848 positionable in first and second passages 816, 818 of connecting member 812 from a lower surface thereof.

A coupling member 850 is positionable in receptacles 832, 820 and 842 of members 830, 812, 840, respectively, when stacked one upon the other. Each of the receptacles 832, 820, 842 communicate with the exterior perimeter of members 830, 812, 840, and include a hole 833, 813, 843 alignable with holes 861, 871, 881, respectively, provided along coupling member 850. Engagement members 860, 870, 880, in the form of set screws or other suitable fastener, are positioned in the aligned holes and engage coupling member 850 to respective ones of the members 830, 812, 840. Coupling member 850 can be recessed in receptacles 832, 820, 840 so that it does not protrude from members 812, 830, 840. Coupling member 850 resists axial displacement of members 830, 840 away from connecting member 812.

Figure 32:
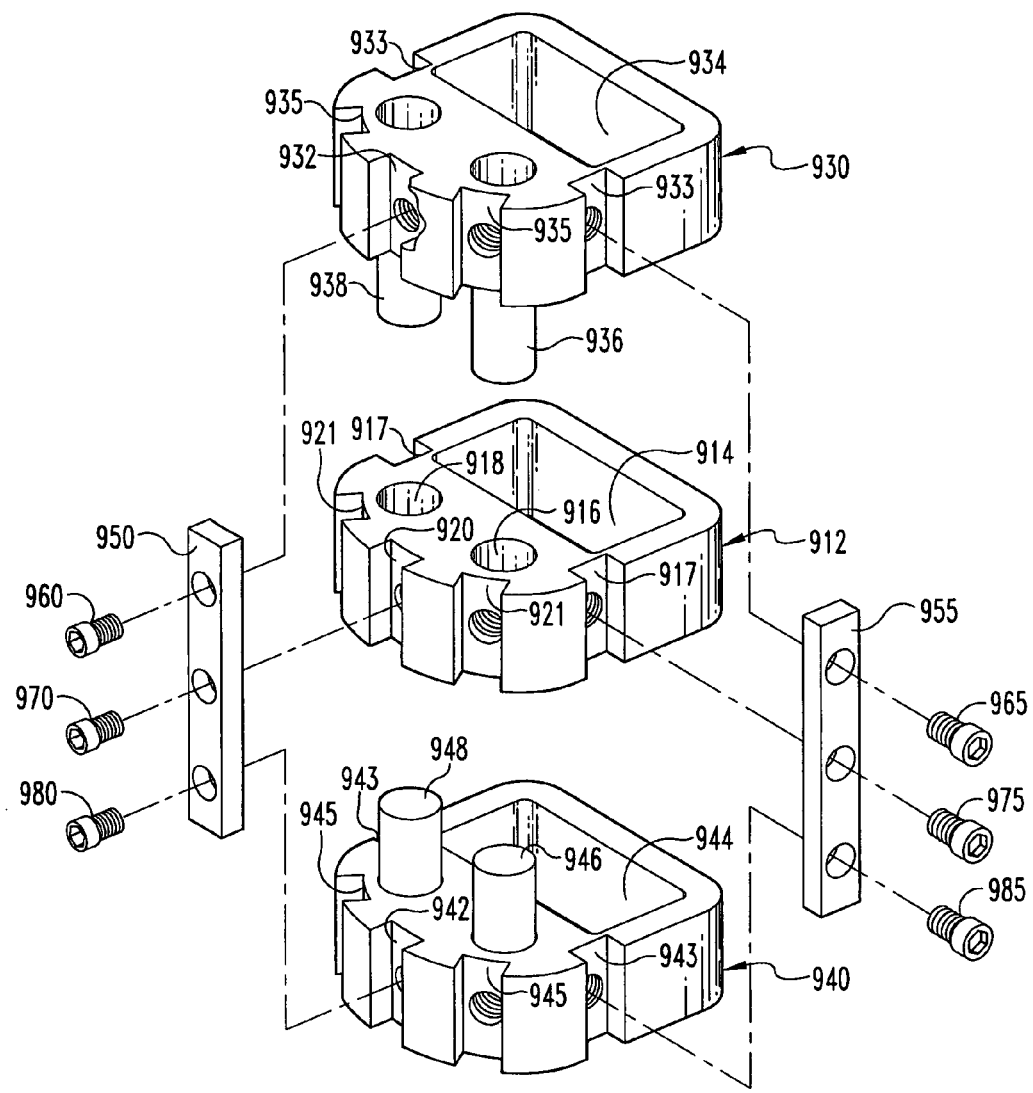
FIG. 32 is an exploded perspective view of another embodiment vertebral replacement device.

In FIG. 32, another embodiment vertebral replacement device 910 is shown with a connecting member 912 and upper and lower members 930, 940. Connecting member 912 and upper and lower members 930, 940 can include a D-shaped body with the convexly curved wall anteriorly oriented between the adjacent vertebrae. Chambers 914, 934, 944 are alignable when stacked to provide a passage for bony fusion. Other shapes and configurations for members 912, 930, 940 are also contemplated as discussed herein.

Connecting member 912 includes first and second passages 916, 918 extending between upper and lower bearing surfaces of connecting member 912. First and second passages 916, 918 are sized and shaped to receive first and second extensions 936, 938 of upper member 930 when upper member 930 is stacked thereon. The pair of extensions 936, 938 resist lateral and torsional movement of upper member 930 relative to connecting member 912. Similarly, lower member 940 includes first and second extensions 946, 948 positionable in first and second passages 916, 918 of connecting member 912 from a lower surface thereof.

A coupling member 950 is positionable in receptacles 932, 920, 942 of members 930, 912, 940, respectively, when stacked one upon the other. Each of the receptacles 932, 920, 942 can include a hole alignable with holes provided along coupling member 950. Engagement members 960, 970, 980, in the form of set screws or other suitable fastener, are positioned in the aligned holes and engage coupling member 950 to respective ones of the members 930, 912, 940.

Coupling member 950 can be recessed in receptacles 932, 920, 942 so that it does not protrude from members 930, 912, 940.

Additional coupling members, such as coupling member 955, can be secured in other receptacles formed about the perimeter of members 930, 912, 940 with engagement members 965, 975, 985, respectively. For example, lateral receptacles 933, 917, 943 can be provided in the opposite side walls of the perimeter of members 930, 912, 940, respectively, to receive coupling members. Oblique receptacles 935, 921, 945 can be provided in the obliquely oriented walls of the perimeter of members 930, 912, 940, respectively, to receive coupling members. Multiple coupling members 950, 955 can be spaced about and secured to the perimeter of members 930, 912, 940 to provide lateral, torsional and axial stability of the stacked members 930, 912, 940.

Figure 33:
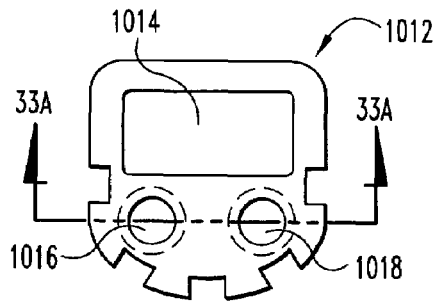
FIGS. 33 and 33A are a plan and section view, respectively, of a first member comprising another embodiment vertebral replacement device.
Figure 34:
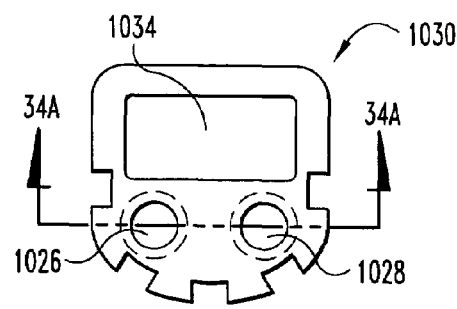
FIGS. 34 and 34A are a plan and section view, respectively, of a second member engageable to the first member of FIGS. 33 and 33A.
Figure 35:
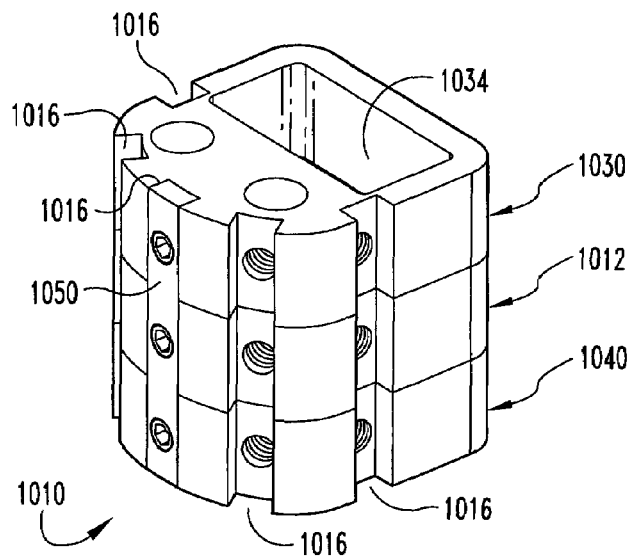
FIG. 35 is a perspective view of a vertebral replacement device comprising the first and second members of FIGS. 33 and 34.

Referring now to FIGS. 33-35, another embodiment stackable vertebral replacement device 1010 is shown with connecting member 1012 and upper and lower members 1030, 1040. Connecting member 1012 and upper and lower members 1030, 1040 can include a D-shaped body with the convexly curved wall anteriorly oriented in the space between adjacent vertebrae. Chambers 1014, 1034 and the chamber (not shown) of lower member 1040 are alignable when stacked to provide a passage for bony fusion. Other shapes and configurations for members 1012, 1030, 1040 are also contemplated as discussed herein.

Figure 33A:
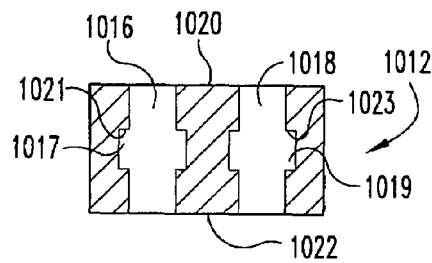

Referring to FIGS. 33 and 33A, connecting member 1012 includes a first receptacle 1016 and a second receptacle 1018 extending between and opening at upper surface 1020 and lower surface 1022 of member 1012. First receptacle 1016 includes a first locking portion 1017 formed therein body 1013, and second receptacle 1018 includes a second locking portion 1019 formed therein.

Figure 34A:
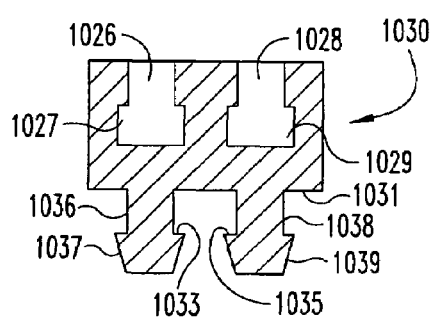

Referring to FIGS. 34-34A, upper member 1030 includes a first extension 1036 and a second extension 1038 extending from lower surface 1031. First extension 1036 includes an engagement member 1037 at a distal end thereof, and second extension 1038 includes an engagement member 1039 at a distal end thereof. First extension 1036 is positionable in first receptacle 1016 so that engagement member 1037 interlocks with first locking portion 1017. Similarly, second extension 1038 is positionable in second receptacle 1018 so that engagement member 1039 interlocks with second locking portion 1019.

In the illustrated embodiment, bearing surfaces 1033, 1035 of engagement members 1037, 1039 bear against surfaces 1021, 1023 of receptacles 1016, 1018, respectively, to resist axial displacement. The interlocking engagement between the engagement members 1037, 1039 and receptacles 1016, 1018 resists axial displacement of upper member 1030 relative to connecting member 1012. The pair of spaced extensions 1036, 1038 resist lateral and torsional displacement of upper member 1030 relative to connecting member 1012. Lower member 1040 can similarly be provided with a pair of extensions having engagement members that are positionable in receptacles 1016, 1018 from lower surface 1012 of connecting member to secure lower member 1040 to connecting member 1012.

Upper member 1030 can be secured to connecting member 1012 to provide a two member stack. Lower member can be secured below connecting member 1012 to provide a three member stack. Upper and lower members 1030, 140 can be provided with receptacles opposite extensions 1036, 1038 to allow stacking and securement of four or more members from one another. For example, as shown in FIGS. 34 and 34A, upper member 1030 includes a first receptacle 1026 having a first locking portion 1027, and a second receptacle 1028 including a second locking portion 1029. A second upper member 1030 can be stacked on upper member 1030 with extensions 1036, 1038 locked in receptacles 1026, 128. Lower member 1040 can be similarly configured with receptacle in its lower surface to facilitate stacking and securement of additional lower members 1040 thereto.

Additional axial securement of the stacked members 1012, 1030, 1040 can provided by coupling member 1050 positionable in any one or combination of receptacles 1016 in the perimeter of the walls of the members, such as discussed above with respect to vertebral replacement device 910. The coupling members 1050 and/or outer receptacles 1016 are not required for axial securement of members 1030, 1040 to connecting member 1012, however, since extensions 1036, 1038 can provide axial securement.

Figure 36:
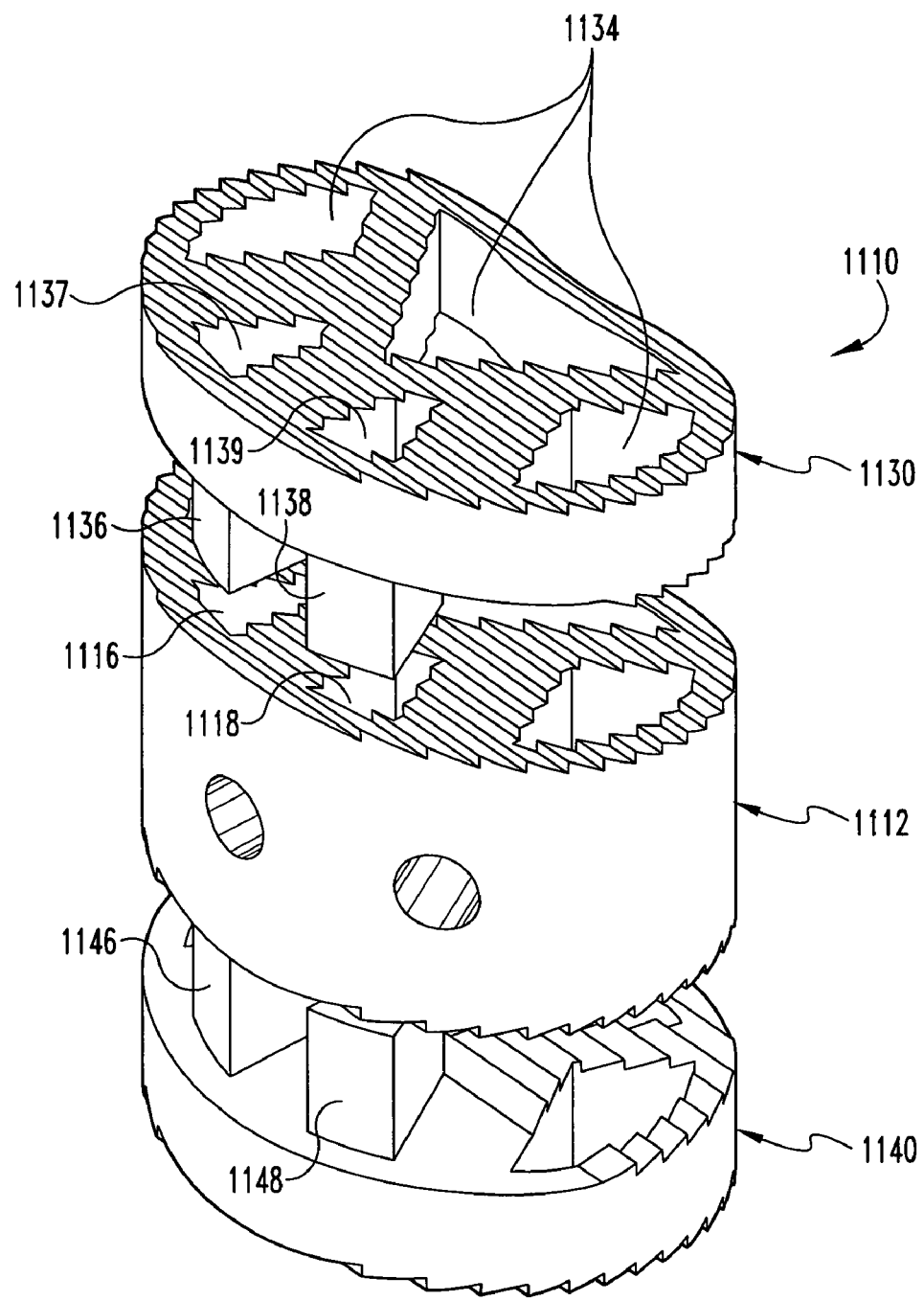
FIG. 36 is an exploded view of another embodiment vertebral replacement device.

Referring now to FIG. 36, another embodiment vertebral replacement device 1110 is shown. Vertebral replacement device 1110 includes an upper member 1130 and a lower member 1140 stackable on opposite sides of connecting member 1112. Connecting member 1112 and upper and lower members 1130, 1140 can include a kidney-shaped body with the convexly curved wall anteriorly oriented in the space between adjacent vertebrae and the concavely curved posterior wall posteriorly oriented. Upper member 1130 includes a number of chambers 1134 therethrough to facilitate bone growth and bony fusion. Connecting member 1112 and lower member 1140 can be provided with similarly sized and shaped chambers alignable with chambers 1134 when members 1130, 1112 and 1140 are stacked one upon the other. Other shapes and configurations for members 1112, 1130, 1140 are also contemplated as discussed herein.

Upper member 1130 includes a first extension 1136 and a second extension 1138 extending from a lower surface thereof. Extensions 1136, 1138 can be integrally formed with upper member 1130. Lower member 1140 includes a first extension 1146 and a second extension 1148 extending from an upper surface thereof. Extensions 1146, 1148 can be integrally formed with lower member 1140. Connecting member 1112 includes receptacles 1116, 1118 extending between upper and lower surfaces thereof to receive corresponding ones of the extensions 1136, 1138 of upper member 1130 and extensions 1146, 1148 of lower member 1140. The interface between the extensions and receptacles resists lateral and torsional movement of upper and lower members 1130, 1140 relative to connecting member 1112. In the illustrated embodiment, the extensions include non-circular cross-sections that are received in the correspondingly shaped receptacles.

The adjacent upper and lower surfaces of the stacked members 1130, 1112, 1140 can include interdigitating ridges to further resist lateral and axial movement. Still other embodiments contemplate the adjacent surfaces can be planar, or can include a telescoping, non-rotatable stacking arrangement between the adjacent members. Axial displacement of the stacked members can be resisted by coupling members engaged along the perimeter of the stacked members, by one or more coupling members extending through all or a portion of the stacked members, or other suitable coupling arrangement.

It is further contemplated that one of the upper or lower members 1130, 1140 can be stacked with connecting member 1112 to provide a two member stack. Upper and lower members 1130, 1140 can also be provided with receptacles 1137, 1139, for example, to receive extensions from a second member to provide a stack of four or more members.

The height and/or angulation between the upper and lower ends of the vertebral replacement device 1110 can thus be adjusted as necessary for disc space replacement or vertebral body replacement procedures. It is also contemplated that connecting member 1112 and/or upper and lower members 1030, 1040 can be provided with a height that enables it to be used in isolation as a disc space replacement device.

In FIGS. 37-46, various shapes for the disc space replacement and/or vertebral body members are illustrated. The members of FIGS. 37-46 can be used in isolation as a disc space replacement member, or provided in a set of multiple members and stacked one upon the other for vertebral replacement procedures. The members can be provided any one or combination of engagement features discussed herein such that when the members are stacked any one or combination of lateral, torsional and axial displacement of the members is resisted.

In FIGS. 37 and 37A, member 1200 includes a D-shaped body having a first end wall 1204, opposite side walls 1208, 1210, and a second end wall 1206. A chamber 1216 is defined between the upper and lower ends of body 1202. Passages 1212, 1214 can extend between the upper lower ends of body 1202 and can be adapted for bone growth, or to receive coupling members or extensions to secure a number of members 1200 in a stack. Second end wall 1206 has a reduced height relative to first end wall 1204 and side walls 1208, 1210 such that body 1202 provides U-shaped upper and lower bearing surfaces 1218, 1220. In one application, first end wall 1204 is oriented anteriorly in the spinal column and side walls 1208, 1210 are laterally spaced to provide bilateral support of the supported vertebra on respective sides of the central axis of the spinal column. First end wall 1204 can include a convexly curved outer surface to fit with the endplate anatomy at the anterior portion of the supported vertebrae. First end wall 1204 also includes a linear inner surface providing end wall 1204 with sufficient thickness for passages 1212, 1214.

In FIG. 38, another embodiment member 1230 includes a D-shaped body 1232 having a first end wall 1234 with a convexly curved outer surface and linear inner surface, opposite side walls 1238, 1240, and a second end wall 1236. A chamber 1246 is defined between the upper and lower ends of body 1232. Passages 1242, 1244 can extend between the upper lower ends of body 1232 and can be adapted for bone growth, or to receive coupling members or extensions to secure a number of members 1230 in a stack. Second end wall 1236 has a reduced height relative to first end wall 1234 and side walls 1238, 1240 such that body 1232 provides U-shaped upper and lower bearing surfaces, such as discussed above with respect to member 1200. Second end wall 1236 is offset anteriorly relative the adjacent ends of side walls 1238, 1240, and extends between side walls 1238, 1240 to provide lateral stability thereto.

In FIG. 39, another embodiment member 1260 includes a U-shaped body 1262 having a first end wall 1264 with a convexly curved outer surface and linear inner surface, and opposite side walls 1268, 1270 that open posteriorly when member 1260 is positioned in the disc space with first end wall 164 anteriorly positioned. A chamber 1276 is defined between the upper and lower surfaces of body 1262 for receipt of bone growth material, a bone graft, or other device or material therein. The open posterior wall further facilitates positioning of body 1262 adjacent the posterior elements of the spinal column without impinging thereon. Passages 1272, 1274 can extend between the upper lower ends of body 1262 through first end wall 1264 and can be adapted for bone growth, or to receive coupling members or extensions to secure a number of members 1260 in a stack.

In FIG. 40, another embodiment member 1300 includes a U-shaped body 1302 having a first end wall 1304 with convexly curved outer and inner surfaces, and opposite side walls 1308, 1310 that open posteriorly when member 1300 is positioned in the disc space and first end wall 1304 is anteriorly positioned. The open posterior portion facilitates positioning of body 1302 adjacent the posterior elements of the spinal column without impinging thereon. A chamber 1316 is defined between the upper and lower ends of body 1300 for receipt of bone growth material, a bone graft, or other device or material therein.

In FIG. 41, another embodiment member 1330 includes a D-shaped body 1332 having a first end wall 1334 with a convexly curved outer surface and linear inner surface, opposite side walls 1338, 1340, and opposite second end wall portions 1336, 1337. A chamber 1346 is defined between the upper and lower ends of body 1332. Passages 1342, 1344 can extend between the upper lower ends of body 1332 through first end wall 1334, and can be adapted for bone growth, or to receive coupling members or extensions to secure a number of members 1330 in a stack. Second end wall portions 1336, 1337 include a space therebetween, and facilitate in maintaining a bone graft or other device or material in chamber 1346. The open second wall further facilitates positioning of body 1332 adjacent the posterior elements of the spinal column without impinging thereon.

In FIG. 42, another embodiment member 1360 includes a semi-circular shaped body 1362 having a first end wall 1364 with a convexly curved inner and outer surfaces and convexly curved side walls 1368, 1370 that open posteriorly when member 1360 is positioned in the disc space with first end wall 1364 anteriorly oriented. A chamber 1376 is defined between the upper and lower ends of body 1360 for receipt of bone growth material, a bone graft, or other device or material therein. Chamber 1376 is open posteriorly of body 1362. The open posterior wall further facilitates positioning of body 1362 adjacent the posterior elements of the spinal column.

In FIG. 43, another embodiment member 1400 includes a body 1402 including a wall 1403 that defines a chamber 1416 having a U-shape. Wall 1403 includes a first end wall portion 1404 with convexly curved inner and outer surfaces. Wall 1403 further includes opposite side wall portions 1408, 1410 extending generally parallel to one another. Wall 1403 further includes a second end wall including a first portion 1406 and a second portion 1407 extending from respective ones of the side wall portions 1410, 1408. Wall 1403 further includes a middle portion 1414 extending into chamber 1416 from first and second portions 1406, 1407 that defines a recess 1418 opening between portions 1406, 1407. The open recess facilitates positioning of member 1400 adjacent the posterior elements of the spinal column without impinging thereon. The number of wall portions provide bearing surface area for supporting the vertebral endplates and a chamber to facilitate fusion of the vertebrae through member 1400.

In FIG. 44, another embodiment member 1430 includes a body 1432 including a first end wall 1434 having a convexly curved outer surface. Passages 1442, 1444 extend through first end wall 1434 between the upper lower ends of body 1432 and can be adapted for bone growth, or to receive coupling members or extensions to secure a number of members 1430 in a stack. Body 1432 further includes opposite side walls 1438, 1440 extending generally parallel to one another. Body 1432 includes a second end wall 1436 having a central convexly curved recess 1437 at a central strut 1447. Central strut 1447 extends between central recess 1437 and first end wall 1434. Central strut 1447 divides body 1432 into a first chamber portion 1445 and a second chamber portion 1446. Recess 1437 facilitates positioning of body 1432 adjacent the posterior elements of the spinal column without impinging thereon.

In FIG. 45, another embodiment member 1460 includes a body 1462 including a first end wall 1464 having a convexly curved outer surface. Body 1462 further includes opposite side walls 1469, 1470 extending generally parallel to one another. Body 1462 includes a second end 1466 having a central recess 1467. A pair of medial walls 1468, 1471 extend anteriorly from second end wall 1466 along central recess 1467. Side wall 1470 and medial wall 1471 define a first chamber 1484, and side wall 1469 and medial wall 1468 define a second chamber 1486. An enlarged recess portion 1472 is located adjacent first end wall 1464 and in communication with narrower portion of recess 1467. Enlarged portion 1472 can receive material to facilitate bone growth, or a coupling member or extensions to secure a number of members 1460 in a stack. Recess 1467 facilitates positioning of body 1462 adjacent the posterior elements of the spinal column without impinging thereon.

In FIG. 46, another embodiment member 1500 includes a body 1502 including a first end wall 1504 having a convexly curved outer surface. Passages 1512, 1514 can extend between the upper lower ends of body 1502 and can be adapted for bone growth, or two receive coupling members or extensions to secure a number of members 1500 in a stack. Body 1502 further includes opposite side walls 1508, 1510 extending generally parallel to one another. Body 1502 includes a second end wall 1506 having a central recess 1507. A pair of medial walls 1517, 1518 extend from second end wall 1506 along central recess 1507 to first end wall 1504. Side wall 1510 and medial wall 1517 define a first chamber 1524, and side wall 1508 and medial wall 1518 define a second chamber 1526. Recess 1507 facilitates positioning of body 1502 adjacent the posterior elements of the spinal column without impinging thereon.

While the invention has been illustrated and described in detail in the drawings and foregoing description, the same is to be considered as illustrative and not restrictive in character. All changes and modifications that come within the spirit of the invention are desired to be protected.

What is claimed is:

1. A vertebral replacement device, comprising:
a first member including a first end and an opposite second end positionable against an endplate of a vertebra, said first member defining a chamber extending between said first end and said second end; and
a second member including a first end and a second end, wherein one of said first member and said second member includes a first receptacle formed in said first end thereof and opening laterally in a wall thereof, and the other of said first member and said second member includes a first extension extending from said first end thereof, wherein said first member is laterally positionable on said second member with said first extension being slidingly received and axially restrained in said first receptacle and engaging said first receptacle to resist axial and rotational displacement of said first member relative to said second member, wherein said first extension includes an enlarged outer end portion tapering toward said first end and said receptacle includes an enlarged inner portion receiving said enlarged outer end portion in dovetail fashion.

2. The device of claim 1, further comprising a second extension opposite said first extension and a second receptacle opposite said first receptacle for slidably receiving said second extension.

3. The device of claim 1, wherein said first member includes a height between said first and second ends adapted to replace a spinal disc space.

4. The device of claim 1, wherein said second member includes a height between said first and second ends adapted to replace a vertebral body.

5. The device of claim 1, wherein:
said first member includes a through-hole extending in a wall thereof between said first end and said second end;
said second member includes a passage extending in a wall thereof from said first end; and
further comprising a coupling member positionable through said through-hole and engageable to said second member in said passage to axially secure said first and second members to one another.

6. The device of claim 5, wherein said first end of said first member includes said extension and a substantially planar bearing surface extending about said chamber at said first end.

7. The device of claim 1, wherein said second member includes a chamber extending therethrough, said chambers being aligned with said first member stacked on said second member.

8. The device of claim 7, further comprising bone growth material in said chamber of each of said first and second members.

9. The device of claim 8, wherein said bone growth material includes one or more selected from group consisting of: bone morphogenetic protein, transforming growth factor 1, insulin-like growth factor 1, platelet-derived growth factor, fibroblast growth factor, and LIM mineralization protein (LMP).

10. The device of claim 8, wherein said bone growth material is provided in a carrier having a form selected from the group consisting of: a sponge, a block, folded sheet, putty, and paste.

11. The device of claim 1, further comprising a third member including a first end positionable against an endplate of a second vertebra and an opposite second end, wherein one of said second member and said third member includes a second receptacle formed in said second end thereof and opening laterally in a wall thereof, and the other of said second member and said third member includes a second extension extending from said second end thereof, wherein said second member is laterally positionable on said third member with said second extension being slidingly received and axially restrained in said second receptacle and engaging said second receptacle to resist axial and rotational displacement of said second member relative to said third member.

12. The device of claim 11, wherein each of said first and second extensions includes an enlarged outer end portion tapering toward said respective first and second ends and each of said first and second receptacles includes an enlarged inner portion receiving said enlarged outer end portion in dovetail fashion.

13. The device of claim 11, wherein said second member includes a chamber extending therethrough, said chambers being aligned with said first member and said third member stacked on said second member.

14. The device of claim 11, wherein:
said first member includes a through-hole extending through a wall thereof between said first end and said second end;
said third member includes a through-hole extending through a wall thereof between said first end and said second end;
said second member includes a first passage in a wall thereof extending therein from said first end and a second passage in a wall thereof extending therein from said second end; and
further comprising a first coupling member positionable through said through-hole of said first member and engageable to said second member in said first passage to axially secure said first and second members to one another and a second coupling member positionable through said through-hole of said third member and engageable to said second member in said second passage to axially secure said second and third members to one another.

15. A vertebral replacement device, comprising:
a first member having a first end and an opposite second end positionable against an endplate of a vertebra, said first member defining a chamber extending between said first and second ends; and
a second member including a first end and a second end, said second member including a chamber extending between said first and second ends, wherein one of said first member and said second member includes a number of receptacles radially formed in and positioned about said first end thereof, and the other of said first member and said second member includes a number of extensions extending radially on and extending axially from said first end thereof in a direction opposite said second end thereof, wherein said first member is positionable on said second member with said first ends oriented toward one another and said number of extensions being received in corresponding ones of said number of receptacles in interdigitating fashion to resist lateral and rotational displacement of said first member relative to said second member, wherein:
said first member includes a through-hole extending in a wall thereof between said first end and said second end;
said second member includes a passage extending in a wall thereof from said first end; and
further comprising a coupling member positionable through said through-hole and engageable to said second member in said passage to axially secure said first and second members to one another.

16. The device of claim 15, wherein said chambers are aligned with said first member stacked on said second member.

17. The device of claim 15, wherein said first member includes a height between said first and second ends adapted to replace a spinal disc space.

18. The device of claim 15, wherein said second member includes a height between said first and second ends adapted to replace a vertebral body.

19. The device of claim 15, further comprising a third member including a first end for engaging an endplate of a second vertebral body and an opposite second end, wherein one of said second member and said third member includes a number of receptacles radially formed in and positioned about said second end thereof, and the other of said second member and said third member includes a number of extensions extending radially from and positioned about said second end thereof, wherein said second member is positionable on said third member with said number of extensions being received in corresponding ones of said number of receptacles and engaging said number of receptacles to resist rotational and lateral displacement of said second member relative to said third member.

20. The device of claim 19, wherein chambers are aligned with said first and third members stacked on said second member.

21. The device of claim 19, wherein:
said third member includes a through-hole extending through a wall thereof between said first end and said second end;
said second member include a second passage in a wall thereof extending therein from said second end; and
further comprising a second coupling member positionable through said through-hole of said third member and engageable to said second member in said second passage to axially secure said second and third members to one another.

22. A vertebral replacement device, comprising:
a first member having a first end and an opposite second end positionable against an endplate of a vertebra, said first member defining a chamber extending between said first and second ends; and
a second member including a first end and a second end, said second member including a chamber extending between said first and second ends, wherein one of said first member and said second member includes a number of receptacles radially formed in and positioned about said first end thereof, and the other of said first member and said second member includes a number of extensions extending radially on and extending axially from said first end thereof in a direction opposite said second end thereof, wherein said first member is positionable on said second member with said first ends oriented toward one another and said number of extensions being received in corresponding ones of said number of receptacles in interdigitating fashion to resist lateral and rotational displacement of said first member relative to said second member, further comprising a flexible engaging member extending between said first and second member, said flexible engaging member engaging an opening in a wall of at least one of said first and second members to axially secure said first and second members to another.

23. The device of claim 22, wherein said flexible engaging member is integrally formed with said second member and is received in said chamber of said first member when said first member is stacked on said second member.

24. The device of claim 23, wherein said second member includes a cylindrical extension extending from said first end of said second member, said cylindrical extension being positionable in said chamber of said first member, wherein said flexible engaging member comprises a portion of said cylindrical extension.

25. The device of claim 24, wherein said flexible engaging member includes an engaging portion extending laterally therefrom releasably engageable to said opening.

26. A vertebral replacement device, comprising:
a first member including a body extending between a first end and an opposite second end positionable toward an endplate of a vertebra, said first member defining a chamber extending between said first end and second ends, said body further including a wall portion adjacent said chamber, said wall portion including first and second holes extending therethrough between said first and second ends; and a second member including a body extending between a first end and a second end, said second member defining a chamber extending between said first and second ends, said body further including a wall portion adjacent said chamber, said wall portion including first and second holes extending therethrough between said first and second ends; and first and second coupling members positionable in respective ones of said first and second holes to axially secure said first member to said second member with said first ends adjacent one another, wherein said first and second coupling members further resist lateral and rotational displacement of said first member relative to said second member.

27. The device of claim 26, wherein said first and second coupling members are screws that threadingly engage at least one of said first and second members.

28. The device of claim 26, wherein said first and second members each include a height between said first and second ends thereof that approximates the height of a spinal disc space.

29. The device of claim 26, wherein one of said first and second members includes a height between said first and second ends thereof that approximates the height of a spinal disc space and the other of said first and second members includes a height between said first and second ends thereof that approximates the height of a vertebral body.

30. The device of claim 26, wherein said second ends of each of said first and second members includes a number of elongated ridges adapted to engage a vertebral endplate.

31. The device of claim 26, wherein said first ends of said first and second members each include a number of elongated ridges that interdigitate when said first member is stacked on said second member.

32. The device of claim 31, wherein said ridges of each of said first and second members each include a peak, a first wall extending from said peak and sloped toward a sidewall of said body, and an opposite second wall extending from said peak and sloped toward said second end of said body.

33. The device of claim 32, wherein:

said first and second ends of said body of said first member diverge from a first side to a second side of said body, said first wall of each of said ridges being oriented toward said first side and said second wall of each of said ridges being oriented toward said second side; and said first and second ends of said body of said second member converge from a first side to a second side of said body, said first wall of said of each of said ridges being oriented toward said second side and said second wall of each of said ridges being oriented toward said first side, wherein when stacked said first side of said first member is aligned with said first side of said second member.

34. The device of claim 32, wherein:

said first and second ends of said body of said first member converge from a first side to a second side of said body, said first wall of each of said ridges being oriented toward said second side and said second wall of each of said ridges being oriented toward said first side; and said first and second ends of said body of said second member converge from a first side to a second side of said body, said first wall of said of each of said ridges being oriented toward said second side and said second wall of each of said ridges being oriented toward said first side, wherein when stacked said second end of said first member and said second end of said second member converge toward one another from said first side to said second side.

35. A vertebral replacement device, comprising:

a first member including a body extending between a first end and an opposite second end positionable toward an endplate of a vertebra, said first member defining a chamber extending between said first end and second ends, said body further including a wall portion adjacent said chamber; and a second member including a body extending between a first end and a second end, said second member defining a chamber extending between said first and second ends, said body further including a wall portion adjacent said chamber, wherein one of said wall portions of said first and second members includes a pair of holes opening toward said first end thereof and the other of said first and second members includes a pair of extensions extending from said first end at said wall portion, said pair of extensions positionable in corresponding ones of said pair of holes when said first member is stacked on said second member with said first ends adjacent one another.

36. The device of claim 35, wherein said extensions are integrally formed with said wall portion of said one of said first and second members.

37. The device of claim 35, wherein said pair of extensions are cylindrical rods.

38. The device of claim 35, wherein said pair of extensions are non-cylindrical and said pair of holes include a non-cylindrical shape adapted to receive said extensions in form fitting engagement.

39. The device of claim 35, wherein said first end of said first member includes a number of elongated ridges extending therealong adapted to interdigitate with a number of elongated ridges extending along said first end of said second member when said first member is stacked thereon.

40. The device of claim 35, wherein said chamber comprises three portions separated from one another by a strut extending between adjacent ones of said chamber portions.

41. The device of claim 35, further comprising a third member including a body extending between a first end and a second end, said first end positionable toward an endplate of a second vertebra, said third member defining a chamber extending between said first and second ends, said body further including a wall portion adjacent said chamber, wherein one of said wall portions of said second and third members includes a pair of holes opening toward said second end thereof and the other of said second and third members includes a pair of extensions extending from said second end at said wall portion, said pair of extensions positionable in corresponding ones of said pair of holes when said third member is stacked on said second member with said second ends adjacent one another.

42. The device of claim 35, wherein each of said extensions includes an engagement member at a distal end thereof and each of said holes includes a locking portion in said body of said other of said first and second members, said engagement members engaging respective ones of said locking portions of said first and second holes to axially secure said first and second members to one another.

43. The device of claim 42, wherein said engagement portion includes an enlarged end portion defining a bearing surface oriented toward said first end of said one of said first and second members and said locking portions each include a locking surface extending about said hole engageable with said bearing surface.

44. The device of claim 35, wherein said first and second members each include a receptacle extending between said first and second ends of said body, said receptacles being aligned with one another when said first member is stacked on said second member, and further comprising, a coupling member positionable in said aligned receptacles and engageable to said first and second members to axially secure said first and second members to one another.

45. The device of claim 44, wherein said receptacles each open along an outer surface of said body of each of said first and second members.

46. The device of claim 44, wherein said body of each of said first and second members includes a number of receptacles extending between said first and second ends positioned about said body and opening along an outer surface of said body, and further comprising a second coupling member positionable in second ones of said receptacles aligned when said first member is stacked on said second member.

47. The device of claim 44, wherein said coupling member is secured in each of said receptacles with a set screw extending through said coupling member and engaging said body of an adjacent one of said first and second members.

48. A vertebral replacement device, comprising:
a first member including a body extending between a first end and an opposite second end positionable toward an endplate of a vertebra, said first member defining a chamber extending between said first and second ends, said body further including a wall portion adjacent said chamber; and
a second member including a body extending between a first end and a second end, said second member defining a chamber extending between said first and second ends, said body further including a wall portion adjacent said chamber, wherein said first and second members each include a receptacle between said first and second ends in said wall portion of said body, said receptacles being aligned when said first member is stacked on said second member, and further comprising a coupling member slidingly received in said aligned receptacles and engageable to each of said first and second members with an engagement member to axially and rotationally secure said first and second members thereto.

49. The device of claim 48, wherein said body of each of said first and second members includes a number of receptacles extending between said first and second ends positioned about said body, and further comprising a second coupling member positionable slidingly received in second ones of said number of receptacles aligned when said first member is stacked on said second member.

50. The device of claim 48, wherein one of said wall portions of said first and second members includes a pair of holes opening toward said first end thereof and the other of said first and second members includes a pair of extensions extending from said first end at said wall portion, said pair of extensions positionable in corresponding ones of said pair of holes when said first member is stacked on said second member with said first ends adjacent one another.

51. A vertebral replacement device, comprising:
a first member including a body extending between a first end and an opposite second end positionable toward an endplate of a vertebra, said first member defining a chamber extending between said first and second ends, said body further including a wall portion adjacent said chamber;
a second member including a body extending between a first end and a second end, said second member defining a chamber extending between said first and second ends, said body further including a wall portion adjacent said chamber, wherein said first and second members each include a receptacle between said first and second ends in said wall portion of said body, said receptacles being aligned when said first member is stacked on said second member, and further comprising a coupling member slidingly received in said aligned receptacles and engageable to each of said first and second members with an engagement member to axially secure said first and second members thereto, wherein said receptacles open along an outer surface of said body of each of said first and second members.

52. A vertebral replacement device, comprising:
a first member including a body extending between a first end and an opposite second end positionable toward an endplate of a vertebra, said first member defining a chamber extending between said first and second ends, said body further including a wall portion adjacent said chamber; and
a second member including a body extending between a first end and a second end, said second member defining a chamber extending between said first and second ends, said body further including a wall portion adjacent said chamber, wherein said first and second members each include a receptacle between said first and second ends in said wall portion of said body, said receptacles being aligned when said first member is stacked on said second member, and further comprising a coupling member slidingly received in said aligned receptacles and engageable to each of said first and second members with an engagement member to axially secure said first and second members thereto, wherein each of said engagement members includes a set screw extending through said coupling member and engaging said body of the adjacent first and second member.

53. A vertebral replacement device, comprising:
a first member extending between a first end and a second end, said second end positionable adjacent a vertebral endplate, said first member including a hole extending therethrough opening at least at said first end;
a second member extending between a first end and a second end, said second member including a hole extending therethrough opening at least at said first end, said first member positionable on said second member with said first ends adjacent one another;
an extension positionable in said holes of said first and second members and extending therebetween when said first member is stacked on said second member; and
a first coupling member extending through said first member and engaging said extension to secure said first member to said extension and a second coupling member extending through said second member and engaging said extension to secure said second member to said extension.

54. The device of claim 53, wherein said hole of said second member opens at said second surface and said extension extends therethrough, further comprising:
a third member extending between a first end a second end, said third member including a hole extending therethrough opening at least at said second end, said third member positionable on said second member with said second ends adjacent one another; and a third coupling member extending through said third member and engaging said extension to secure said third member to said extension.

55. The device of claim 53, wherein said first and second members each include a chamber extending between and opening at said first and second ends thereof.

56. The device of claim 53, wherein:
said first member includes a bore in communication with said hole and opening in a side wall of said first member, said first coupling member positionable in said bore; and said second member includes a bore in communication with said hole and opening in a side wall of said second member, said second coupling member positionable in said bore.

57. A device positionable in a space between vertebrae, comprising:
a body having a first height between upper and lower ends, said body including a first end wall and a pair of opposite side walls, said first end wall including a convexly curved outer surface, said body further comprising a chamber between said end wall and said opposite side walls, wherein said body includes a second end wall opposite said first end wall extending between said opposite side walls, said second end wall including upper and lower ends recessed below said upper and lower ends of said body; and
wherein said first end wall includes a pair of holes extending between and opening at said upper and lower ends.

58. The device of claim 57, wherein said second end wall includes a second height between said upper and lower ends thereof, said second height being less than said first height.

59. The device of claim 57, wherein said opposite side walls are parallel to one another.

60. The device of claim 57, wherein said opposite side walls extend from a first end at said first end wall to an opposite second end, said second wall being offset from said second ends toward said first end wall.

61. A device positionable in a space between vertebrae, comprising:
a body having a height between upper and lower ends, said body including a first end wall and a pair of opposite side walls, said first end wall including a convexly curved outer surface and an inner surface, said body further comprising a chamber between said opposite side walls, wherein said chamber is open between said opposite side walls in a direction opposite said first end wall and said first end wail includes a thickness between said inner surface and said outer surface that is greater than a thickness of said opposite side walls, wherein said opposite side walls each extend from a first end at said first end wall to an opposite second end, said opposite second ends of said opposite side walls extending toward one another.

62. The device of claim 61, wherein said first end wall includes a concavely curved inner surface.

63. The device of claim 61, wherein said first end wall includes a linear inner surface.

64. A device positionable in a space between vertebrae, comprising:
a body having a height between upper and lower ends said body including a first end wall and a pair of opposite side walls, said first end wall including a convexly curved outer surface and an inner surface, said body further comprising a chamber between said opposite side walls, wherein said chamber is open between said opposite side walls in a direction opposite said first end wall and said first end wall includes a thickness between said inner surface and said outer surface that is greater than a thickness of said opposite side walls, wherein said first end wall includes a pair of holes extending between and opening at said upper and lower ends.

65. The device of claim 64, wherein said opposite side walls each extend from a first end at said first end wall to an opposite second end, said opposite second ends of said opposite side walls extending toward one another.

66. A device positionable in a space between vertebrae, comprising:
a body having a height between upper and lower ends, said body including a first end wall, a second end wall, and a pair of opposite side walls extending therebetween, said body further comprising a chamber between said first and second end walls and said opposite side walls, said body further including a pair of medial walls between said opposite side walls extending from said second end wall toward said first end wall, wherein said recess includes an enlarged portion adjacent said first end wall.

67. The device of claim 66, wherein said medial walls extend from said second end wall to a third wall adjacent said first end wall, said medial walls and said third wall forming a recess opening through said second end wall.

68. The device of claim 66, wherein said medial walls extend from said second wall to said first end wall.

69. The device of claim 68, wherein said chamber comprises:
a first portion formed between said first end wall, one of said side walls, one of said medial walls, and said second end wall; and
a second portion formed between said first end wall, the other of said side walls, the other of said medial walls, and said second end wall.

70. The device of claim 69, wherein said first end wall includes a pair of holes extending between and opening at said upper and lower ends.

71. The device of claim 69, wherein said body forms a recess between said medial walls, said recess opening through said second end wall.

72. A device positionable in a space between vertebrae, comprising:
a body having a height between upper and lower ends, said body including a first end wall, a second end wall, and a pair of opposite side wails extending therebetween, said body further comprising a chamber between said first and second end wails and said opposite side walls, said body further comprising a medial wall between said opposite side walls extending through said chamber from said first end wall to said second end wall, wherein said second end wall includes a concavely curved outer surface portion at said medial wall, and linear outer surface portions extending from said concavely outer surface portion to respective ones of said opposite side walls.

73. The device of claim 72, wherein said first end wall includes a convexly curved outer surface.

74. The device of claim 72, wherein said first end wall includes a pair of holes extending between and opening at said upper and lower ends.

75. A vertebral replacement device, comprising:
- a first member extending between a first end and a second end, said first member including a chamber opening at least at said first end, and said second end positionable toward an adjacent vertebra;
- a second member extending between a first end and a second end, said second member including a chamber opening at least at said first end; and
- a sleeve extending between said first and second members and positionable in said chambers thereof opening at said first ends, wherein said first and second members are slidable along said sleeve, said sleeve including at least one flexible engaging member thereof for engaging the adjacent first member or second member thereto when said first member is stacked on said second member.

76. The device of claim 75, wherein said sleeve is hollow and opens at each of said ends thereof.

77. The device of claim 75, wherein said chamber of said first member opens at said second end.

78. The device of claim 75, wherein said chamber of said second member opens at said first end, said sleeve extends through said second end, and further comprising a third member stackable against said second end of said second member, said sleeve including a flexible engaging member engaging said third member to said first and second members.

79. The device of claim 75, wherein said chamber of said second member opens at said first end, and further comprising:
- a third member stackable against said second end of said second member, said third member including a chamber extending between first and second ends thereof, and
- a second sleeve positionable in said chambers of said second and third members through said second ends thereof, said sleeve including at least one flexible engaging member engaging said third member to said second member.

80. A vertebral replacement device, comprising:
- a first member having a first end and an opposite second end positionable against an endplate of a vertebra, said first member defining a chamber extending between said first and second ends; and
- a second member including a first end and a second end, said second member including a chamber extending between said first and second ends, wherein one of said first member and said second member includes a number of receptacles radially formed in and positioned about said first end thereof, and the other of said first member and said second member includes a number of extensions extending radially on and extending axially from said first end thereof in a direction opposite said second end thereof, wherein said first member is positionable on said second member with said first ends oriented toward one another and said number of extensions being received in corresponding ones of said number of receptacles in interdigitating fashion to resist lateral and rotational displacement of said first member relative to said second member, wherein said number of extensions are V-shaped and taper away from said first end and said number of receptacles are V-shaped and taper from said first end toward said second end.

* * * * *